US006703199B1

(12) United States Patent
Koide

(10) Patent No.: US 6,703,199 B1
(45) Date of Patent: Mar. 9, 2004

(54) ARTIFICIAL ANTIBODY POLYPEPTIDES

(75) Inventor: Shohei Koide, Rochester, NY (US)

(73) Assignee: Research Corporation Technologies, Inc., Tucson, AZ (US)

(*) Notice: Subject to any disclaimer, the term of this patent is extended or adjusted under 35 U.S.C. 154(b) by 126 days.

(21) Appl. No.: 09/637,614

(22) Filed: Aug. 11, 2000

Related U.S. Application Data

(62) Division of application No. 09/096,749, filed on Jun. 12, 1998.
(60) Provisional application No. 60/049,410, filed on Jun. 12, 1997.

(51) Int. Cl.[7] .......................... C12Q 1/68; C12P 21/06; C07K 1/00; C07H 21/02

(52) U.S. Cl. .................. 435/6; 435/69.1; 435/DIG. 23; 435/DIG. 24; 536/23.1; 536/23.4; 536/23.53; 530/300; 530/350

(58) Field of Search .............................. 435/5, 6, 320.1, 435/DIG. 23, DIG. 24, 69.1; 536/23.1, 23.4, 23.53, 24.1, 23.5; 530/300, 350

(56) References Cited

U.S. PATENT DOCUMENTS 6,348,584 B1 * 2/2002 Hodgson et al. ............ 536/23.5

FOREIGN PATENT DOCUMENTS

| WO | WO-94/24278 | 10/1994 | ........... C12N/15/09 |
| WO | WO 95/27045 | 10/1995 | ............ C12N/9/00 |

OTHER PUBLICATIONS

Baron, M., et al., "Protein modules", *TIBS*, vol. 16, 13–17, (Jan. 1991).
Bazan, J.F., "Structural design and molecular evolution of a cytokine receptor superfamily", *Proc. Natl. Acad. Sci. USA*, vol. 87, 6934–6938, (Sep. 1990).
Bork, P., et al., "Review: The Immunoglobulin Fold—Structural Classification, Sequence Patterns and Common Core", *J. Mol. Biol.*, vol. 242, 309–320, (1994).
Burgess, W.H., et al., "Possible Dissociation of the Heparin–binding and Mitogenic Activities of Heparin–binding (Acidic Fibroblast) Growth Factor–1 from Its Receptor–binding Activities by Site Directed Mutagensis of a Single Lysine Residue", *The Journal of Cell Biology*, 111, 2129–2138, (Nov. 1992).
Campbell, I.C., et al., "Building proteins with fibronectin type III modules", *Structure*, vol. 2, 333–337, (May 15, 1994).
Cota, E., et al., "Two proteins with the same structure respond very differently to mutation: The role of plasticity in protein stability", *J. Mol. Biol.*, vol. 302, 713–725, (2000).
Doolittle, R.F., "The multiplicity of domains in proteins", *Annu. Rev. Biochem.*, vol. 64, 287–314, (1995).

Green, S.M., et al., "Contributions of the polar, uncharged amino acids to the stability of staphylococcal nuclease: Evidence for mutational effects on the free eneregy of the denatured state", *Biochemistry*, vol. 31, No. 25, 5717–5728, (1992).
Grumet, M., et al., "Structure of a New Nervous System Glycoprotein, Nr–CAM, and Its Relationship to Subgroups of Neural Cell Adhesion Molecules", *the Journal of Cell Biology*, 113, 1399–1412, (Jun., 1991).
Helms, L.R., et al., "Destabilizing loop swaps in the CDRs of an immunoglobulin Vl domain", *Protein Science*, vol. 4, 2073–2081, (1995).
Holm, L., et al., "FSSP: select structural neighbours of 1fnf", *Science*, 273 (5275) : 595–60 fssp//1fnf.fssp, 3 pages, (1996).
Lazar, E., et al., "Transforming Growth Factor alpha: Mutation of Aspartic Acid 47 and Leucine 48 Results in Different Biological Activites", *Molecular and Cellular Biology*, 8, 1247–1252, (Mar., 1988).
Lin, M.C., et al., "Structural Function Relationships in Glucagon: properties of highly purified Des–His1–, monoiodo–, and [Des–Asn28–, thr29] (homoserine lactone27) –glucagon", *Biochemistry*, vol. 14, No. 8, 1559–1563, (1975).
Marti-Renom, M.A., et al., "Comparative protein structure modeling of genes and genomes", *Annu. Rev. Biophys. Biomol. Struct.*, vol. 29, 291–325, (2000).
Matthews, B.W., "Structural and genetic analysis of protein stability", *Annu. Rev. Biochem.*, vol. 62, 139–60, (1993).
Schiweck, W., et al., "The rational construction of an antibody against cystatin: Lessons from the crystal structure of an artificial Fab fragment", *J. Mol. Biol.*, vol. 268, 934–951, (1997).
Schwartz, G.P., et al., "A superactive insulin: [B10–Aspartic acid] insulin(human)", *Proc. Nat'l. Acad. Sci. USA*, vol. 84, 6408–6411, (1987).
Shortle, D., et al., "Contributions of the large hydrophobic amino acids to the stability of staphylococcal nuclease", *Biochemistry*, vol. 29, 8033–8041, (1990).
Desiderio, A., et al., "A semi–synthetic repertoire of intrinsically stable antibody fragments derived from a single–framework scaffold", *J. Mol. Biol.*, vol. 310, pp. 603–615, (2001).

(List continued on next page.)

Primary Examiner—Padmashri Ponnaluri
(74) Attorney, Agent, or Firm—Schwegman, Lundberg, Woessner & Kluth, P.A.

(57) ABSTRACT

A fibronectin type III (Fn3) polypeptide monobody, a nucleic acid molecule encoding said monobody, and a variegated nucleic acid library encoding said monobody, are provided by the invention. Also provided are methods of preparing a Fn3 polypeptide monobody, and kits to perform said methods. Further provided is a method of identifying the amino acid sequence of a polypeptide molecule capable of binding to a specific binding partner (SBP) so as to form a polypeptide:SSP complex, and a method of identifying the amino acid sequence of a polypeptide molecule capable of catalyzing a chemical reaction with a catalyzed rate constant, $k_{cat}$, and an uncatalyzed rate constant, $k_{uncat}$, such that the ratio of $k_{cat}/k_{uncat}$ is greater than 10.

3 Claims, 19 Drawing Sheets

OTHER PUBLICATIONS

Holm, L., et al., "Mapping the protein universe", *Science*, vol. 273, p. 595–602, (Aug. 2, 1996).

Koide, A., et al., "The fibronectin type III domain as a scaffold for novel binding proteins", *J. Mol. Biol.*, vol. 284, pp. 1141–1151, (1998).

Shusta, E.V., et al., "Directed evolution of a stable scaffold for T–cell receptor engineering", *Nature Biotechnology*, vol. 18, pp. 754–759, (Jul. 2000).

van den Beucken, T., "Building novel binding ligands to B7.1 and B7.2 based on human antibody single variable light chain domains", *J. Mol. Biol.*, vol. 310, pp. 591–601, (2001).

Ely, Kathryn R., et al., "Common molecular scaffold for two unrelated RGD molecules", *Protein Engineering*, vol. 8, No. 8,(1995),823–827.

Van Den Beucken, Twan, et al., "Building novel binding ligands to B7.1 and B7.2 based on human antibody single variable light chain domains", *J. Mol. Biol*, vol. 310,(2001), 591–601.

Winter, Greg, "Making Antibodies by Phage Displa Technology", *Ann. Rev. Immunol.*, *12*, (1994),433–455.

* cited by examiner

FIG. 1A
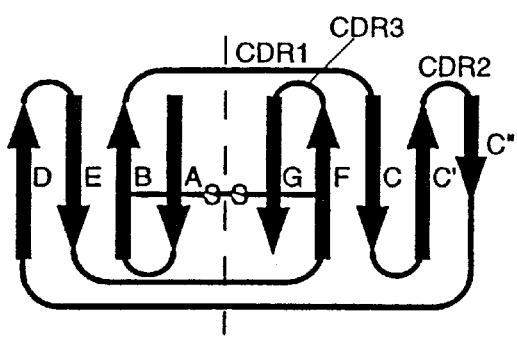
Immunoglobulin VH
FIG. 1B
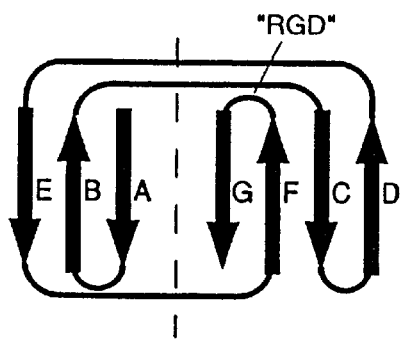
Fibronectin type III
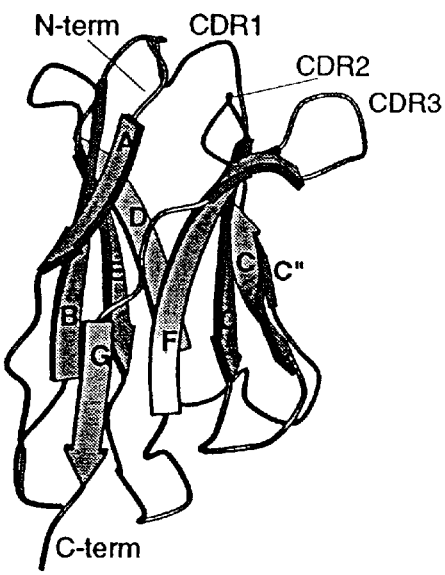
FIG. 1C
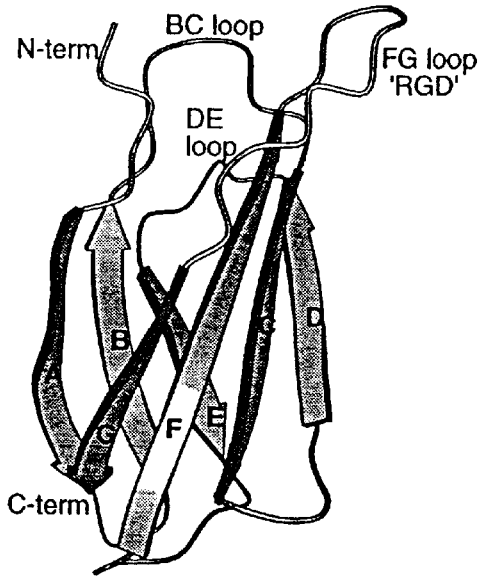
FIG. 1D

```
NdeI                              PstI                              EcoRI
   1         11         21          31         41
mq VSDVPRDLEV VAATPTSLLI SWDAPAVTVR YYRITYGETG GNSPVQEFTV
             A        B                     C            D

SalI                 SacI              XhoI
  51         61         71         81         91
   PGSKSTATIS GLKPGVDYTI TVYAVTGRGD SPASSKPISI NYRT
         E           F                       G
```

FIG. 2

```
NdeI
CATATGCAGGTTTCTGATGTTCCGCGTGACCTGGAAGTTGTTGCTGCGACCCCGACTAGC
    MetGlnValSerAspValProArgAspLeuGluValValAlaAlaThrProThrSer
   -2 -1  1                         10              A
```

```
        BclI PvuII        PstI   BC loop                        BsiWI
   CTGCTGATCAGCTGGGATGCTCCTGCAGTTACCGTGCGTTATTACCGTATCACGTACGGT
   LeuLeuIleSerTrpAspAlaProAlaValThrValArgTyrTyrArgIleThrTyrGly
            20       B                30                      C
```

```
                          EcoRI
   GAAACCGGTGGTAACTCCCCGGTTCAGGAATTCACTGTACCTGGTTCCAAGTCTACTGCT
   GluThrGlyGlyAsnSerProValGlnGluPheThrValProGlySerLysSerThrAla
        40               D     50                              E
```

```
                  SalI          Bst1107I
   ACCATCAGCGGCCTGAAACCGGGTGTCGACTATACCATCACTGTATACGCTGTTACTGGC
   ThrIleSerGlyLeuLysProGlyValAspTyrThrIleThrValTyrAlaValThrGly
        60                         70           F
```

```
      FG loop        SacI                                      XhoI
   CGTGGTGACAGCCCAGCGAGCTCCAAGCCAATCTCGATTAACTACCGTACCTAGTAACTC
   ArgGlyAspSerProAlaSerSerLysProIleSerIleAsnTyrArgThr
            80                       90       G
```

FIG. 5

ARTIFICIAL ANTIBODY POLYPEPTIDES

This application is a divisional of U.S. Ser. No. 09/096,749, filed Jun. 12, 1998, which claims priority under 35 U.S.C. 119(e) to provisional application U.S. Ser. No. 60/049,410, filed Jun. 12, 1997. These applications are incorporated herein by reference.

FIELD OF THE INVENTION

The present invention relates generally to the field of the production and selection of binding and catalytic polypeptides by the methods of molecular biology, using both combinatorial chemistry and recombinant DNA. The invention specifically relates to the generation of both nucleic acid and polypeptide libraries derived therefrom encoding the molecular scaffolding of Fibronectin Type III (Fn3) modified in one or more of its loop regions. The invention also relates to the "artificial mini-antibodies" or "monobodies," i.e., the polypeptides comprising an Fn3 scaffold onto which loop regions capable of binding to a variety of different molecular structures (such as antibody binding sites) have been grafted.

BACKGROUND OF THE INVENTION

Antibody Structure

A standard antibody (Ab) is a tetrameric structure consisting of two identical immunoglobulin (Ig) heavy chains and two identical light chains. The heavy and light chains of an Ab consist of different domains. Each light chain has one variable domain (VL) and one constant domain (CL), while each heavy chain has one variable domain (VH) and three or four constant domains (CH) (Alzari et al., 1988). Each domain, consisting of ~110 amino acid residues, is folded into a characteristic β-sandwich structure formed from two β-sheets packed against each other, the immunoglobulin fold. The VH and VL domains each have three complementarity determining regions (CDR1–3) that are loops, or turns, connecting β-strands at one end of the domains (FIG. 1: A, C). The variable regions of both the light and heavy chains generally contribute to antigen specificity, although the contribution of the individual chains to specificity is not always equal. Antibody molecules have evolved to bind to a large number of molecules by using six randomized loops (CDRs). However, the size of the antibodies and the complexity of six loops represents a major design hurdle if the end result is to be a relatively small peptide ligand.

Antibody Substructures

Functional substructures of Abs can be prepared by proteolysis and by recombinant methods. They include the Fab fragment, which comprises the VH-CH1 domains of the heavy chain and the VL-CL1 domains of the light chain joined by a single interchain disulfide bond, and the Fv fragment, which comprises only the VH and VL domains. In some cases, a single VH domain retains significant affinity (Ward et al., 1989). It has also been shown that a certain monomeric κ light chain will specifically bind to its cognate antigen. (L. Masat et al., 1994). Separated light or heavy chains have sometimes been found to retain some antigen-binding activity (Ward et al., 1989). These antibody fragments are not suitable for structural analysis using NMR spectroscopy due to their size, low solubility or low conformational stability.

Another functional substructure is a single chain Fv (scFv), comprised of the variable regions of the immunoglobulin heavy and light chain, covalently connected by a peptide linker (S-z Hu et al., 1996). These small (M, 25,000) proteins generally retain specificity and affinity for antigen in a single polypeptide and can provide a convenient building block for larger, antigen-specific molecules. Several groups have reported biodistribution studies in xenografted athymic mice using scFv reactive against a variety of tumor antigens, in which specific tumor localization has been observed. However, the short persistence of scFvs in the circulation limits the exposure of tumor cells to the scFvs, placing limits on the level of uptake. As a result, tumor uptake by scFvs in animal studies has generally been only 1–5% ID/g as opposed to intact antibodies that can localize in tumors ad 30–40% ID/g and have reached levels as high as 60–70% ID/g.

A small protein scaffold called a "minibody" was designed using a part of the Ig VH domain as the template (Pessi et al., 1993). Minibodies with high affinity (dissociation constant $(K_d) \sim 10^{-7}$ M) to interleukin-6 were identified by randomizing loops corresponding to CDR1 and CDR2 of VH and then selecting mutants using the phage display method (Martin et al., 1994). These experiments demonstrated that the essence of the Ab function could be transferred to a smaller system. However, the minibody had inherited the limited solubility of the VH domain (Bianchi et al., 1994).

It has been reported that camels (*Camelus dromedarius*) often lack variable light chain domains when IgG-like material from their serum is analyzed, suggesting that sufficient antibody specificity and affinity can be derived form VH domains (three CDR loops) alone. Davies and Riechmann recently demonstrated that "camelized" VH domains with high affinity $(K_d \sim 10^{-7}$ M) and high specificity can be generated by randomizing only the CDR3. To improve the solubility and suppress nonspecific binding, three mutations were introduced to the framework region (Davies & Riechmann, 1995). It has not been definitively shown, however, that camelization can be used, in general, to improve the solubility and stability of VHs.

An alternative to the "minibody" is the "diabody." Diabodies are small bivalent and bispecific antibody fragments, i.e., they have two antigen-binding sites. The fragments comprise a heavy-chain variable domain ($V_H$) connected to a light-chain variable domain ($V_L$) on the same polypeptide chain ($V_H$-$V_L$). Diabodies are similar in size to an Fab fragment. By using a linker that is too short to allow pairing between the two domains on the same chain, the domains are forced to pair with the complementary domains of another chain and create two antigen-binding sites. These dimeric antibody fragments, or "diabodies," are bivalent and bispecific. P. Holliger et al., PNAS 90:6444–6448 (1993).

Since the development of the monoclonal antibody technology, a large number of 3D structures of Ab fragments in the complexed and/or free states have been solved by X-ray crystallography (Webster et al., 1994; Wilson & Stanfield, 1994). Analysis of Ab structures has revealed that five out of the six CDRs have limited numbers of peptide backbone conformations, thereby permitting one to predict the backbone conformation of CDRs using the so-called canonical structures (Lesk & Tramontano, 1992; Rees et al., 1994). The analysis also has revealed that the CDR3 of the VH domain (VH-CDR3) usually has the largest contact surface and that its conformation is too diverse for canonical structures to be defined; VH-CDR3 is also known to have a large variation in length (Wu et al., 1993). Therefore, the structures of crucial regions of the Ab-antigen interface still need to be experimentally determined.

Comparison of crystal structures between the free and complexed states has revealed several types of conformational rearrangements. They include side-chain rearrangements, segmental movements, large rearrangements of VH-CDR3 and changes in the relative position of the VH and VL domains (Wilson & Stanfield, 1993). In the free state, CDRs, in particular those which undergo large conformational changes upon binding, are expected to be flexible. Since X-ray crystallography is not suited for characterizing flexible parts of molecules, structural studies in the solution state have not been possible to provide dynamic pictures of the conformation of antigen-binding sites.

Mimicking the Antibody-binding Site

CDR peptides and organic CDR mimetics have been made (Dougall et al., 1994). CDR peptides are short, typically cyclic, peptides which correspond to the amino acid sequences of CDR loops of antibodies. CDR loops are responsible for antibody-antigen interactions. Organic CDR mimetics are peptides corresponding to CDR loops which are attached to a scaffold, e.g., a small organic compound.

CDR peptides and organic CDR mimetics have been shown to retain some binding affinity (Smyth & von Itzstein, 1994). However, as expected, they are too small and too flexible to maintain full affinity and specificity. Mouse CDRs have been grafted onto the human Ig framework without the loss of affinity (Jones et al., 1986; Riechmann et al., 1988), though this "humanization" does not solve the above-mentioned problems specific to solution studies.

Mimicking Natural Selection Processes of Abs

In the immune system, specific Abs are selected and amplified from a large library (affinity maturation). The processes can be reproduced in vitro using combinatorial library technologies. The successful display of Ab fragments on the surface of bacteriophage has made it possible to generate and screen a vast number of CDR mutations (McCafferty et al., 1990; Barbas et al., 1991; Winter et al., 1994). An increasing number of Fabs and Fvs (and their derivatives) is produced by this technique, providing a rich source for structural studies. The combinatorial technique can be combined with Ab mimics.

A number of protein domains that could potentially serve as protein scaffolds have been expressed as fusions with phage capsid proteins. Review in Clackson & Wells, Trends Biotechnol. 12:173–184 (1994). Indeed, several of these protein domains have already been used as scaffolds for displaying random peptide sequences, including bovine pancreatic trypsin inhibitor (Roberts et al., PNAS 89:2429–2433 (1992)), human growth hormone (Lowman et al., Biochemistry 30:10832–10838 (1991)), Venturini et al., Protein Peptide Letters 1:70–75 (1994)), and the IgG binding domain of Streptococcus (O'Neil et al., Techniques in Protein Chemistry V (Crabb, L,. ed.) pp. 517–524, Academic Press, San Diego (1994)). These scaffolds have displayed a single randomized loop or region.

Researchers have used the small 74 amino acid α-amylase inhibitor Tendamistat as a presentation scaffold on the filamentous phage M13 (McConnell and Hoess, 1995). Tendamistat is a β-sheet protein from *Streptomyces tendae*. It has a number of features that make it an attractive scaffold for peptides, including its small size, stability, and the availability of high resolution NMR and X-ray structural data. Tendamistat's overall topology is similar to that of an immunoglobulin domain, with two β-sheets connected by a series of loops. In contrast to immunoglobulin domains, the β-sheets of Tendamistat are held together with two rather than one disulfide bond, accounting for the considerable stability of the protein. By analogy with the CDR loops found in immunoglobulins, the loops the Tendamistat may serve a similar function and can be easily randomized by in vitro mutagenesis.

Tendamistat, however, is derived from *Streptomyces tendae*. Thus, while Tendamistat may be antigenic in humans, its small size may reduce or inhibit its antigenicity. Also, Tendamistat's stability is uncertain. Further, the stability that is reported for Tendamistat is attributed to the presence of two disulfide bonds. Disulfide bonds, however, are a significant disadvantage to such molecules in that they can be broken under reducing conditions and must be properly formed in order to have a useful protein structure. Further, the size of the loops in Tendamistat are relatively small, thus limiting the size of the inserts that can be accommodated in the scaffold. Moreover, it is well known that forming correct disulfide bonds in newly synthesized peptides is not straightforward. When a protein is expressed in the cytoplasmic space of *E. coli*, the most common host bacterium for protein overexpression, disulfide bonds are usually not formed, potentially making it difficult to prepare large quantities of engineered molecules.

Thus, there is an on-going need for small, single-chain artificial antibodies for a variety of therapeutic, diagnostic and catalytic applications.

SUMMARY OF THE INVENTION

The invention provides a fibronectin type III (Fn3) polypeptide monobody comprising a plurality of Fn3 β-strand domain sequences that are linked to a plurality of loop region sequences. One or more of the monobody loop region sequences of the Fn3 polypeptide vary by deletion, insertion or replacement of at least two amino acids from the corresponding loop region sequences in wild-type Fn3. The β-strand domains of the monobody have at least about 50% total amino acid sequence homology to the corresponding amino acid sequence of wild-type Fn3's β-strand domain sequences. Preferably, one or more of the loop regions of the monobody comprise amino acid residues:

i) from 15 to 16 inclusive in an AB loop;
ii) from 22 to 30 inclusive in a BC loop;
iii) from 39 to 45 inclusive in a CD loop;
iv) from 51 to 55 inclusive in a DE loop;
v) from 60 to 66 inclusive in an EF loop; and
vi) from 76 to 87 inclusive in an FG loop.

The invention also provides a nucleic acid molecule encoding a Fn3 polypeptide monobody of the invention, as well as an expression vector comprising said nucleic acid molecule and a host cell comprising said vector.

The invention further provides a method of preparing a Fn3 polypeptide monobody. The method comprises providing a DNA sequence encoding a plurality of Fn3 β-strand domain sequences that are linked to a plurality of loop region sequences, wherein at least one loop region of said sequence contains a unique restriction enzyme site. The DNA sequence is cleaved at the unique restriction site. Then a preselected DNA segment is inserted into the restriction site. The preselected DNA segment encodes a peptide capable of binding to a specific binding partner (SBP) or a transition state analog compound (TSAC). The insertion of the preselected DNA segment into the DNA sequence yields a DNA molecule which encodes a polypeptide monobody having an insertion. The DNA molecule is then expressed so as to yield the polypeptide monobody.

Also provided is a method of preparing a Fn3 polypeptide monobody, which method comprises providing a replicatable DNA sequence encoding a plurality of Fn3 β-strand domain sequences that are linked to a plurality of loop region sequences, wherein the nucleotide sequence of at least one loop region is known. Polymerase chain reaction (PCR) primers are provided or prepared which are sufficiently complementary to the known loop sequence so as to be hybridizable under PCR conditions, wherein at least one of the primers contains a modified nucleic acid sequence to be inserted into the DNA sequence. PCR is performed using the replicatable DNA sequence and the primers. The reaction product of the PCR is then expressed so as to yield a polypeptide monobody.

The invention further provides a method of preparing a Fn3 polypeptide monobody. The method comprises providing a replicatable DNA sequence encoding a plurality of Fn3 β-strand domain sequences that are linked to a plurality of loop region sequences, wherein the nucleotide sequence of at least one loop region is known. Site-directed mutagenesis of at least one loop region is performed so as to create an insertion mutation. The resultant DNA comprising the insertion mutation is then expressed.

Further provided is a variegated nucleic acid library encoding Fn3 polypeptide monobodies comprising a plurality of nucleic acid species encoding a plurality of Fn3 β-strand domain sequences that are linked to a plurality of loop region sequences, wherein one or more of the monobody loop region sequences vary by deletion, insertion or replacement of at least two amino acids from corresponding loop region sequences in wild-type Fn3, and wherein the β-strand domains of the monobody have at least a 50% total amino acid sequence homology to the corresponding amino acid sequence of β-strand domain sequences of the wild-type Fn3. The invention also provides a peptide display library derived from the variegated nucleic acid library of the invention. Preferably, the peptide of the peptide display library is displayed on the surface of a bacteriophage, e.g., a M13 bacteriophage or a fd bacteriophage, or virus.

The invention also provides a method of identifying the amino acid sequence of a polypeptide molecule capable of binding to a specific binding partner (SBP) so as to form a polypeptide:SSP complex, wherein the dissociation constant of the said polypeptide:SBP complex is less than $10^{-6}$ moles/liter. The method comprises the steps of:
  a) providing a peptide display library of the invention;
  b) contacting the peptide display library of (a) with an immobilized or separable SBP;
  c) separating the peptide:SBP complexes from the free peptides;
  d) causing the replication of the separated peptides of (c) so as to result in a new peptide display library distinguished from that in (a) by having a lowered diversity and by being enriched in displayed peptides capable of binding the SBP;
  e) optionally repeating steps (b), (c), and (d) with the new library of (d); and
  f) determining the nucleic acid sequence of the region encoding the displayed peptide of a species from (d) and hence deducing the peptide sequence capable of binding to the SBP.

The present invention also provides a method of preparing a variegated nucleic acid library encoding Fn3 polypeptide monobodies having a plurality of nucleic acid species each comprising a plurality of loop regions, wherein the species encode a plurality of Fn3 β-strand domain sequences that are linked to a plurality of loop region sequences, wherein one or more of the loop region sequences vary by deletion, insertion or replacement of at least two amino acids from corresponding loop region sequences in wild-type Fn3, and wherein the β-strand domain sequences of the monobody have at least a 50% total amino acid sequence homology to the corresponding amino acid sequences of β-strand domain sequences of the wild-type Fn3, comprising the steps of
  a) preparing an Fn3 polypeptide monobody having a predetermined sequence;
  b) contacting the polypeptide with a specific binding partner (SBP) so as to form a polypeptide:SSP complex wherein the dissociation constant of the said polypeptide:SBP complex is less than $10^{-6}$ moles/liter;
  c) determining the binding structure of the polypeptide:SBP complex by nuclear magnetic resonance spectroscopy or X-ray crystallography; and
  d) preparing the variegated nucleic acid library, wherein the variegation is performed at positions in the nucleic acid sequence which, from the information provided in (c), result in one or more polypeptides with improved binding to the SBP.

Also provided is a method of identifying the amino acid sequence of a polypeptide molecule capable of catalyzing a chemical reaction with a catalyzed rate constant, $k_{cat}$, and an uncatalyzed rate constant, $k_{uncat}$, such that the ratio of $k_{cat}/k_{uncat}$ is greater than 10. The method comprises the steps of:
  a) providing a peptide display library of the invention;
  b) contacting the peptide display library of (a) with an immobilized or separable transition state analog compound (TSAC) representing the approximate molecular transition state of the chemical reaction;
  c) separating the peptide:TSAC complexes from the free peptides;
  d) causing the replication of the separated peptides of (c) so as to result in a new peptide display library distinguished from that in (a) by having a lowered diversity and by being enriched in displayed peptides capable of binding the TSAC;
  e) optionally repeating steps (b), (c), and (d) with the new library of (d); and
  f) determining the nucleic acid sequence of the region encoding the displayed peptide of a species from (d) and hence deducing the peptide sequence.

The invention also provides a method of preparing a variegated nucleic acid library encoding Fn3 polypeptide monobodies having a plurality of nucleic acid species each comprising a plurality of loop regions, wherein the species encode a plurality of Fn3 β-strand domain sequences that are linked to a plurality of loop region sequences, wherein one or more of the loop region sequences vary by deletion, insertion or replacement of at least two amino acids from corresponding loop region sequences in wild-type Fn3, and wherein the β-strand domain sequences of the monobody have at least a 50% total amino acid sequence homology to the corresponding amino acid sequences of β-strand domain sequences of the wild-type Fn3, comprising the steps of
  a) preparing an Fn3 polypeptide monobody having a predetermined sequence, wherein the polypeptide is capable of catalyzing a chemical reaction with a catalyzed rate constant, $k_{cat}$, and an uncatalyzed rate constant, $k_{uncat}$, such that the ratio of $k_{cat}/k_{uncat}$ is greater than 10;
  b) contacting the polypeptide with an immobilized or separable transition state analog compound (TSAC) representing the approximate molecular transition state of the chemical reaction;
  c) determining the binding structure of the polypeptide:TSAC complex by nuclear magnetic resonance spectroscopy or X-ray crystallography; and d) preparing the variegated nucleic acid library, wherein the variegation is performed at positions in the nucleic acid sequence which, from the information provided in (c), result in one or more polypeptides with improved binding to or stabilization of the TSAC.

The invention also provides a kit for the performance of any of the methods of the invention. The invention further provides a composition, e.g., a polypeptide, prepared by the use of the kit, or identified by any of the methods of the invention.

The following abbreviations have been used in describing amino acids, peptides, or proteins: Ala, or A, Alanine; Arg, or R, Arginine; Asn or N, asparagine; Asp, or D, aspartic acid; Cysor C, cystein; Gln, or Q, glutamine; Glu, or E, glutamic acid; Gly, or G, glycine; His, or H, histidine; Ile, or I, isoleucine; Leu, or L, leucine; Lys, or K, lysine; Met, or M, methionine; Phe, or F, phenylalanine; Pro, or P, proline; Ser, or S, serine; Thr, or T, threonine; Trp, or W, tryptophan; Tyr, or Y, tyrosine; Val, or V, valine.

The following abbreviations have been used in describing nucleic acids, DNA, or RNA: A, adenosine; T, thymidine; G, guanosine; C, cytosine.

BRIEF DESCRIPTION OF THE DRAWINGS

FIG. 1A. β-Strand and loop topology of anti-lysozyme immunoglobulin D1.3. (Bhat et al., 1994). The locations of complementarity determining regions (CDRs, hypervariable regions) are indicated.

FIG. 1B. β-Strand and loop topology of the 10th type III domain of human fibronectin. (Main et al., 1992) The locations of the integrin-binding Arg-Gly-Asp (RGD) sequence is indicated.

FIG. 1C. MOLSCRIPT representation of anti-lysozyme immunoglobulin D1.3. (Fraulis, 1991; Bhat et al., 1994) The locations of complementarity determining regions (CDRs, hypervariable regions) are indicated.

FIG. 1D. MOLSCRIPT representation of the 10th type III domain of human fibronectin. (Kraulis, 1991; Main et al., 1992) The locations of the integrin-binding Arg-Gly-Asp (RGD) sequence is indicated.

FIG. 2. Amino acid sequence (SEQ ID NO: 110) and restriction sites of the synthetic Fn3 gene. The residue numbering is according to Main et al. (1992). Restriction enzyme sites designed are shown above the amino acid sequence. β-Strands are denoted by underlines. The N-terminal "mq" sequence has been added for a subsequent cloning into an expression vector. The His•tag (Novagen) fusion protein has an additional sequence, MGSSHHHH-HHSSGLVPRGSH (SEQ ID NO:114), preceding the Fn3 sequence shown above.

FIG. 5. Designed Fn3 gene showing DNA and amino acid sequences (SEQ ID NO:111 and SEQ ID NO:112). The amino acid numbering is according to Main et al. (1992). The two loops that were randomized in combinatorial libraries are enclosed in boxes.

DETAILED DESCRIPTION OF THE INVENTION

Figure 3A:
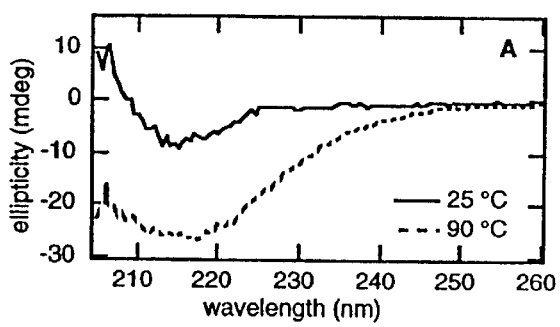
FIG. 3A. Far UV CD spectra of wild-type Fn3 at 25° C. and 90° C. Fn3 (50 μM) was dissolved in sodium acetate (50 mM, pH 4.6).

For the past decade the immune system has been exploited as a rich source of de novo catalysts. Catalytic antibodies have been shown to have chemoselectivity, enantioselectivity, large rate accelerations, and even an ability to reroute chemical reactions. In most cases the antibodies have been elicited to transition state analog (TSA) haptens. These TSA haptens are stable, low-molecular weight compounds designed to mimic the structures of the energetically unstable transition state species that briefly (approximate half-life $10^{-13}$ s) appear along reaction pathways between reactants and products. Anti-TSA antibodies, like natural enzymes, are thought to selectively bind and stabilize transition state, thereby easing the passage of reactants to products. Thus, upon binding, the antibody lowers the energy of the actual transition state and increases the rate of the reaction. These catalysts can be programmed to bind to geometrical and electrostatic features of the transition state so that the reaction route can be controlled by neutralizing unfavorable charges, overcoming entropic barriers, and dictating stereoelectronic features of the reaction. By this means even reactions that are otherwise highly disfavored have been catalyzed (Janda et al. 1997). Further, in many instances catalysts have been made for reactions for which there are no known natural or manmade enzymes.

The success of any combinatorial chemical system in obtaining a particular function depends on the size of the library and the ability to access its members. Most often the antibodies that are made in an animal against a hapten that mimics the transition state of a reaction are first screened for binding to the hapten and then screened again for catalytic activity. An improved method allows for the direct selection for catalysis from antibody libraries in phage, thereby linking chemistry and replication.

A library of antibody fragments can be created on the surface of filamentous phage viruses by adding randomized antibody genes to the gene that encodes the phage's coat protein. Each phage then expresses and displays multiple copies of a single antibody fragment on its surface. Because each phage possesses both the surface-displayed antibody fragment and the DNA that encodes that fragment, and antibody fragment that binds to a target can be identified by amplifying the associated DNA.

Immunochemists use as antigens materials that have as little chemical reactivity as possible. It is almost always the case that one wishes the ultimate antibody to interact with native structures. In reactive immunization the concept is just the opposite. One immunizes with compounds that are highly reactive so that upon binding to the antibody molecule during the induction process, a chemical reaction ensues. Later this same chemical reaction becomes part of the mechanism of the catalytic event. In a certain sense one is immunizing with a chemical reaction rather than a substance per se. Reactive immunogens can be considered as analogous to the mechanism-based inhibitors that enzymologists use except that they are used in the inverse way in that, instead of inhibiting a mechanism, they induce a mechanism.

Man-made catalytic antibodies have considerable commercial potential in many different applications. Catalytic antibody-based products have been used successfully in prototype experiments in therapeutic applications, such as prodrug activation and cocaine inactivation, and in non-therapeutic applications, such as biosensors and organic synthesis.

Catalytic antibodies are theoretically more attractive than noncatalytic antibodies as therapeutic agents because, being catalytic, they may be used in lower doses, and also because their effects are unusually irreversible (for example, peptide bond cleavage rather than binding). In therapy, purified catalytic antibodies could be directly administered to a patient, or alternatively the patient's own catalytic antibody response could be elicited by immunization with an appropriate hapten. Catalytic antibodies also could be used as clinical diagnostic tools or as regioselective or stereoselective catalysts in the synthesis of fine chemicals.

I. Mutation of Fn3 Loops and Grafting of Ab Loops onto Fn3

An ideal scaffold for CDR grafting is highly soluble and stable. It is small enough for structural analysis, yet large enough to accommodate multiple CDRs so as to achieve tight binding and/or high specificity.

A novel strategy to generate an artificial Ab system on the framework of an existing non-Ab protein was developed. An advantage of this approach over the minimization of an Ab scaffold is that one can avoid inheriting the undesired properties of Abs. Fibronectin type III domain (Fn3) was used as the scaffold. Fibronectin is a large protein which plays essential roles in the formation of extracellular matrix and cell-cell interactions; it consists of many repeats of three types (I, II and III) of small domains (Baron et al., 1991). Fn3 itself is the paradigm of a large subfamily (Fn3 family or s-type Ig family) of the immunoglobulin superfamily (IgSF). The Fn3 family includes cell adhesion molecules, cell surface hormone and cytokine receptors, chaperoning, and carbohydrate-binding domains (for reviews, see Bork & Doolittle, 1992; Jones, 1993; Bork et al., 1994; Campbell & Spitzfaden, 1994; Harpez & Chothia, 1994).

Recently, crystallographic studies revealed that the structure of the DNA binding domains of the transcription factor NF-kB is also closely related to the Fn3 fold (Ghosh et al., 1995; Müller et al., 1995). These proteins are all involved in specific molecular recognition, and in most cases ligand-binding sites are formed by surface loops, suggesting that the Fn3 scaffold is an excellent framework for building specific binding proteins. The 3D structure of Fn3 has been determined by NMR (Main et al., 1992) and by X-ray crystallography (Leahy et al., 1992; Dickinson et al., 1994). The structure is best described as a β-sandwich similar to that of Ab VH domain except that Fn3 has seven β-strands instead of nine (FIG. 1). There are three loops on each end of Fn3; the positions of the BC, DE and FG loops approximately correspond to those of CDRI, 2 and 3 of the VH domain, respectively (FIGS. 1C, D).

Fn3 is small (~95 residues), monomeric, soluble and stable. It is one of few members of IgSF that do not have disulfide bonds; VH has an interstrand disulfide bond (FIG. 1A) and has marginal stability under reducing conditions. Fn3 has been expressed in E. coli (Aukhil et al., 1993). In addition, 17 Fn3 domains are present just in human fibronectin, providing important information on conserved residues which are often important for the stability and folding (for sequence alignment, see Main et al., 1992 and Dickinson et al., 1994). From sequence analysis, large variations are seen in the BC and FG loops, suggesting that the loops are not crucial to stability. NMR studies have revealed that the FG loop is highly flexible; the flexibility has been implicated for the specific binding of the 10th Fn3 to $\alpha_5\beta_1$ integrin through the Arg-Gly-Asp (RGD) (SEQ ID NO:113) motif In the crystal structure of human growth hormone-receptor complex (de Vos et al., 1992), the second Fn3 domain of the receptor interacts with hormone via the FG and BC loops, suggesting it is feasible to build a binding site using the two loops.

The tenth type III module of fibronectin has a fold similar to that of immunoglobulin domains, with seven β strands forming two antiparallel β sheets, which pack against each other (Main et al., 1992). The structure of the type II module consists of seven β strands, which form a sandwich of two antiparallel β sheets, one containing three strands (ABE) and the other four strands (C'CFG) (Williams et al., 1988). The triple-stranded β sheet consists of residues Glu-9-Thr-14 (A), Ser-17-Asp-23 (B), and Thr-56-Ser-60 (E). The majority of the conserved residues contribute to the hydrophobic core, with the invariant hydrophobic residues Trp-22 and Try-68 lying toward the N-terminal and C-terminal ends of the core, respectively. The β strands are much less flexible and appear to provide a rigid framework upon which functional, flexible loops are built. The topology is similar to that of immunoglobulin C domains.

Gene Construction and Mutagenesis

A synthetic gene for tenth Fn3 of human fibronectin (FIG. 2) was designed which includes convenient restriction sites for ease of mutagenesis and uses specific codons for high-level protein expression (Gribskov et al., 1984).

Figure 7:
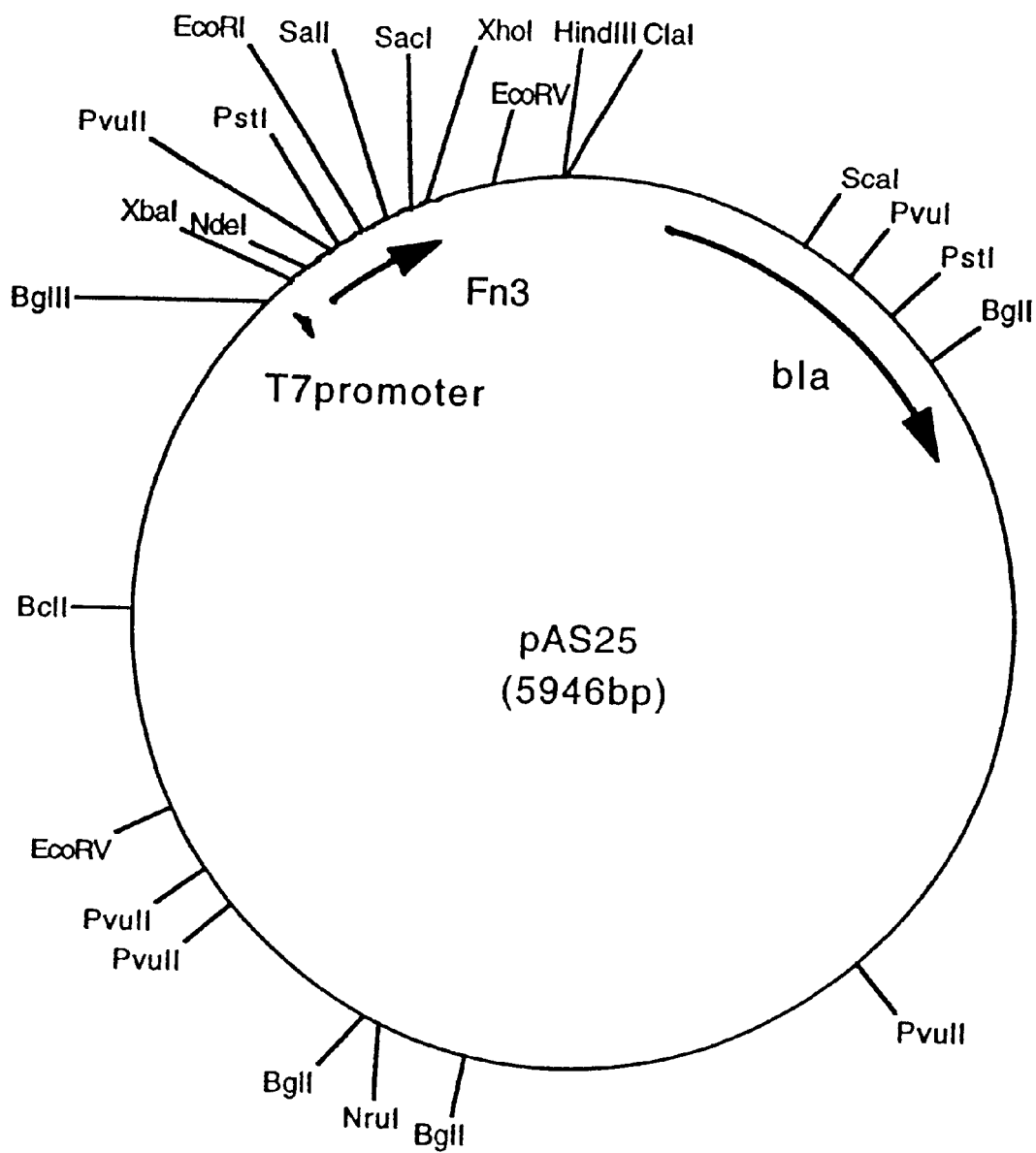
FIG. 7. Map of plasmid pAS25. Plasmid pAS25 is the expression vector of Fn3.

The gene was assembled as follows: (1) the gene sequence was divided into five parts with boundaries at designed restriction sites (FIG. 2); (2) for each part, a pair of oligonucleotides that code opposite strands and have complementary overlaps of ~15 bases was synthesized; (3) the two oligonucleotides were annealed and single strand regions were filled in using the Klenow fragment of DNA polymerase; (4) the double-stranded oligonucleotide was cloned into the pET3a vector (Novagen) using restriction enzyme sites at the termini of the fragment and its sequence was confirmed by an Applied Biosystems DNA sequencer using the dideoxy termination protocol provided by the manufacturer; (5) steps 2–4 were repeated to obtain the whole gene (plasmid pAS25) (FIG. 7).

Although the present method takes more time to assemble a gene than the one-step polymerase chain reaction (PCR) method (Sandhu et al., 1992), no mutations occurred in the gene. Mutations would likely have been introduced by the low fidelity replication by Taq polymerase and would have required time-consuming gene editing. The gene was also cloned into the pET15b (Novagen) vector (pEW1). Both vectors expressed the Fn3 gene under the control of bacteriophage T7 promoter (Studler et al. 1990); pAS25 expressed the 96-residue Fn3 protein only, while pEWI expressed Fn3 as a fusion protein with poly-histidine peptide (His•tag). Recombinant DNA manipulations were performed according to Molecular Cloning (Sambrook et al., 1989), unless otherwise stated.

Mutations were introduced to the Fn3 gene using either cassette mutagenesis or oligonucleotide site-directed mutagenesis techniques (Deng & Nickoloff, 1992). Cassette mutagenesis was performed using the same protocol for gene construction described above; double-stranded DNA fragment coding a new sequence was cloned into an expression vector (pAS25 and/or pEW1). Many mutations can be made by combining a newly synthesized strand (coding mutations) and an oligonucleotide used for the gene synthesis. The resulting genes were sequenced to confirm that the designed mutations and no other mutations were introduced by mutagenesis reactions.

Design and Synthesis of Fn3 Mutants with Antibody CDRs

Figure 4A:
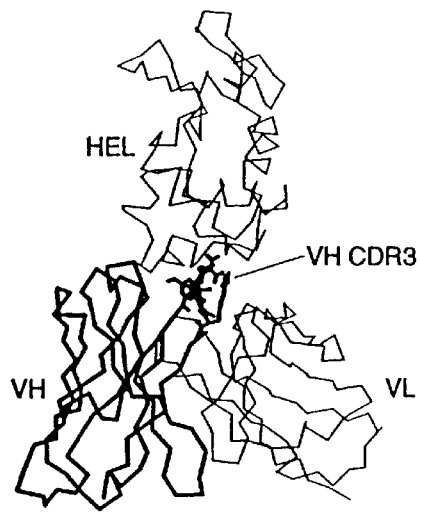
FIG. 4A. Cα trace of the crystal structure of the complex of lysozyme (HEL) and the Fv fragment of the anti-hen egg-white lysozyme (anti-HEL) antibody D1.3 (Bhat et al., 1994). Side chains of the residues 99–102 of VH CDR3, which make contact with HEL, are also shown.

Two candidate loops (FG and BC) were identified for grafting. Antibodies with known crystal structures were examined in order to identify candidates for the sources of loops to be grafted onto Fn3. Anti-hen egg lysozyme (HEL) antibody D1.3 (Bhat et al., 1994) was chosen as the source of a CDR loop. The reasons for this choice were: (1) high resolution crystal structures of the free and complexed states are available (FIG. 4A; Bhat et al., 1994), (2) thermodynamics data for the binding reaction are available (Tello et al., 1993), (3) D1.3 has been used as a paradigm for Ab structural analysis and Ab engineering (Verhoeyen et al., 1988; McCafferty et al., 1990) (4) site-directed mutagenesis experiments have shown that CDR3 of the heavy chain (VH-CDR3) makes a larger contribution to the affinity than the other CDRs (Hawkins et al., 1993), and (5) a binding assay can be easily performed. The objective for this trial was to graft VH-CDR3 of D1.3 onto the Fn3 scaffold without significant loss of stability.

Figure 4B:
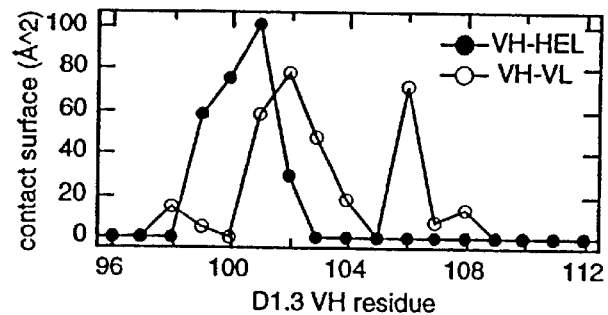
FIG. 4B. Contact surface area for each residue of the D1.3 VH-HEL and VH-VL interactions plotted vs. residue number of D1.3 VH. Surface area and secondary structure were determined using the program DSSP (Kabsh and Sander, 1983).
Figure 4C:
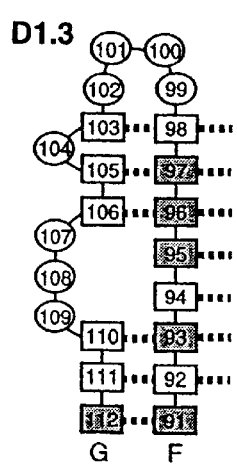
FIG. 4C. Schematic drawings of the β-sheet structure of the F strand-loop-G strand moieties of D1.3 VH. The boxes denote residues in β-strands and ovals those not in strands. The shaded boxes indicate residues of which side chains are significantly buried. The broken lines indicate hydrogen bonds.
Figure 4D:
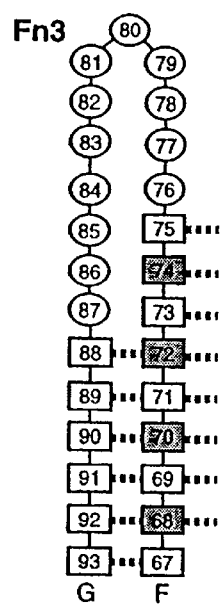
FIG. 4D. Schematic drawings of the β-sheet structure of the F strand-loop-G strand moieties of Fn3. The boxes denote residues in β-strands and ovals those not in strands. The shaded boxes indicate residues of which side chains are significantly buried. The broken lines indicate hydrogen bonds.

An analysis of the D1.3 structure (FIG. 4) revealed that only residues 99–102 ("RDYR") make direct contact with hen egg-white lysozyme (HEL) (FIG. 4B), although VH-CDR3 is defined as longer (Bhat et al., 1994). It should be noted that the C-terminal half of VH-CDR3 (residues 101–104) made significant contact with the VL domain (FIG. 4B). It has also become clear that D1.3 VH-CDR3 (FIG. 4C) has a shorter turn between the strands F and G than the FG loop of Fn3 (FIG. 4D). Therefore, mutant sequences were designed by using the RDYR (99–102) of D1.3 as the core and made different boundaries and loop lengths (Table 1). Shorter loops may mimic the D1.3 CDR3 conformation better, thereby yielding higher affinity, but they may also significantly reduce stability by removing wild-type interactions of Fn3.

TABLE 1

Amino acid sequences of D 1.3 VH CDR3, VH8 CDR3 and Fn3 FG loop and list of planned mutants.

| 96 | 100 | 105 |
|----|-----|-----|
| •  | •   | •   |

TABLE 1-continued

Amino acid sequences of D 1.3 VH CDR3, VH8 CDR3 and Fn3 FG loop
and list of planned mutants.

```
D1.3    A R E R D Y R L D Y W G Q G
            (SEQ ID NO:1)
VH8     A R G A V V S Y Y A M D Y W G Q G
            (SEQ ID NO:2)
                75        80        85
                 •         •         •
Fn3     Y A V T G R G D S P A S S K P I
            (SEQ ID NO:3)
```

Mutant Sequence

```
                                                (SEQ ID NO:4)
D1.3-1  Y A E R D Y R L D Y - - - - P I
                                                (SEQ ID NO:5)
D1.3-2  Y A V R D Y R L D Y - - - - P I
                                                (SEQ ID NO:6)
D1.3-3  Y A V R D Y R L D Y A S S K P I
                                                (SEQ ID NO:7)
D1.3-4  Y A V R D Y R L D Y - - - K P I
                                                (SEQ ID NO:8)
D1.3-5  Y A V R D Y R - - - - - S K P I
                                                (SEQ ID NO:9)
D1.3-6  Y A V T R D Y R L - - S S K P I
                                                (SEQ ID NO:10)
D1.3-7  Y A V T E R D Y R L - S S K P I
                                                (SEQ ID NO:11)
VH8-1   Y A V A V V S Y Y A M D Y - P I
                                                (SEQ ID NO:12)
VH8-2   Y A V T A V V S Y Y A S S K P I
```

Underlines indicate residues in β-strands. Bold characters indicate replaced residues.

In addition, an anti-HEL single VH domain termed VH8 (Ward et al., 1989) was chosen as a template. VH8 was selected by library screening and, in spite of the lack of the VL domain, VH8 has an affinity for HEL of 27 nM, probably due to its longer VH-CDR3 (Table 1). Therefore, its VH-CDR3 was grafted onto Fn3. Longer loops may be advantageous on the Fn3 framework because they may provide higher affinity and also are close to the loop length of wild-type Fn3. The 3D structure of VH8 was not known and thus the VH8 CDR3 sequence was aligned with that of D1.3 VH-CDR3; two loops were designed (Table 1).

Mutant Construction and Production

Site-directed mutagenesis experiments were performed to obtain designed sequences. Two mutant Fn3s, D1.3-1 and D1.3-4 (Table 1) were obtained and both were expressed as soluble His-tag fusion proteins. D1.34 was purified and the His.tag portion was removed by thrombin cleavage. D1.3-4 is soluble up to at least 1 mM at pH 7.2. No aggregation of the protein has been observed during sample preparation and NMR data acquisition.

Protein Expression and Purification

*E. coli* BL21 (DE3) (Novagen) were transformed with an expression vector (pAS25, pEW1 and their derivatives) containing a gene for the wild-type or a mutant. Cells were grown in M9 minimal medium and M9 medium supplemented with Bactotrypton (Difco) containing ampicillin (200 μg/ml). For isotopic labeling, $^{15}N$ $NH_4Cl$ and/or $^{13}C$ glucose replaced unlabeled components. 500 mL medium in a 2 liter baffle flask were inoculated with 10 ml of overnight culture and agitated at 37° C. Isopropylthio-β-galactoside (IPTG) was added at a final concentration of 1 mM to initiate protein expression when OD (600 nm) reaches one. The cells were harvested by centrifugation 3 hours after the addition of IPTG and kept frozen at −70° C. until used.

Fn3 without His•tag was purified as follows. Cells were suspended in 5 ml/(g cell) of Tris (50 mM, pH 7.6) containing ethylenediaminetetraacetic acid (EDTA; 1 mM) and phenylmethylsulfonyl fluoride (1 mM). HEL was added to a final concentration of 0.5 mg/ml. After incubating the solution for 30 minutes at 37° C., it was sonicated three times for 30 seconds on ice. Cell debris was removed by centrifugation. Ammonium sulfate was added to the solution and precipitate recovered by centrifugation. The pellet was dissolved in 5–10 ml sodium acetate (50 mM, pH 4.6) and insoluble material was removed by centrifugation. The solution was applied to a SEPHACRYL S1000HR column (Pharmacia) equilibrated in the sodium acetate buffer. Fractions containing Fn3 then was applied to a RESOURCES® column (Pharmacia) equilibrated in sodium acetate (50 mM, pH 4.6) and eluted with a linear gradient of sodium chloride (0–0.5 M). The protocol can be adjusted to purify mutant proteins with different surface charge properties.

Fn3 with His•tag was purified as follows. The soluble fraction was prepared as described above, except that sodium phosphate buffer (50 mM, pH 7.6) containing sodium chloride (100 mM) replaced the Tris buffer. The solution was applied to a HI-TRAP chelating column (Pharmacia) preloaded with nickel and equilibrated in the phosphate buffer. After washing the column with the buffer, His•tag-Fn3 was eluted in the phosphate buffer containing 50 mM EDTA. Fractions containing His•tag-Fn3 were pooled and applied to a SEPHACRYL S100-HR column, yielding highly pure protein. The His•tag portion was cleaved off by treating the fusion protein with thrombin using the protocol supplied by Novagen. Fn3 was separated from the His•tag peptide and thrombin by a RESOURCES® column using the protocol above.

The wild-type and two mutant proteins so far examined are expressed as soluble proteins. In the case that a mutant is expressed as inclusion bodies (insoluble aggregate), it is first examined if it can be expressed as a soluble protein at lower temperature (e.g., 25–30° C.). If this is not possible, the inclusion bodies are collected by low-speed centrifugation following cell lysis as described above. The pellet is washed with buffer, sonicated and centrifuged. The inclusion bodies are solubilized in phosphate buffer (50 mM, pH 7.6) containing guanidinium chloride (GdnCl, 6 M) and will be loaded on a HI-TRAP chelating column. The protein is eluted with the buffer containing GdnCl and 50 mM EDTA.

Conformation of Mutant Fn3, D1.3-4

The $^1H$ NMR spectra of His•tag D1.3-4 fusion protein closely resembled that of the wild-type, suggesting the mutant is folded in a similar conformation to that of the wild-type. The spectrum of D1.3-4 after the removal of the His•tag peptide showed a large spectral dispersion. A large dispersion of amide protons (7–9.5 ppm) and a large number of downfield (5.0–6.5 ppm) $C^\alpha$ protons are characteristic of a sheet protein (Wütithrich, 1986).

Figure 12:
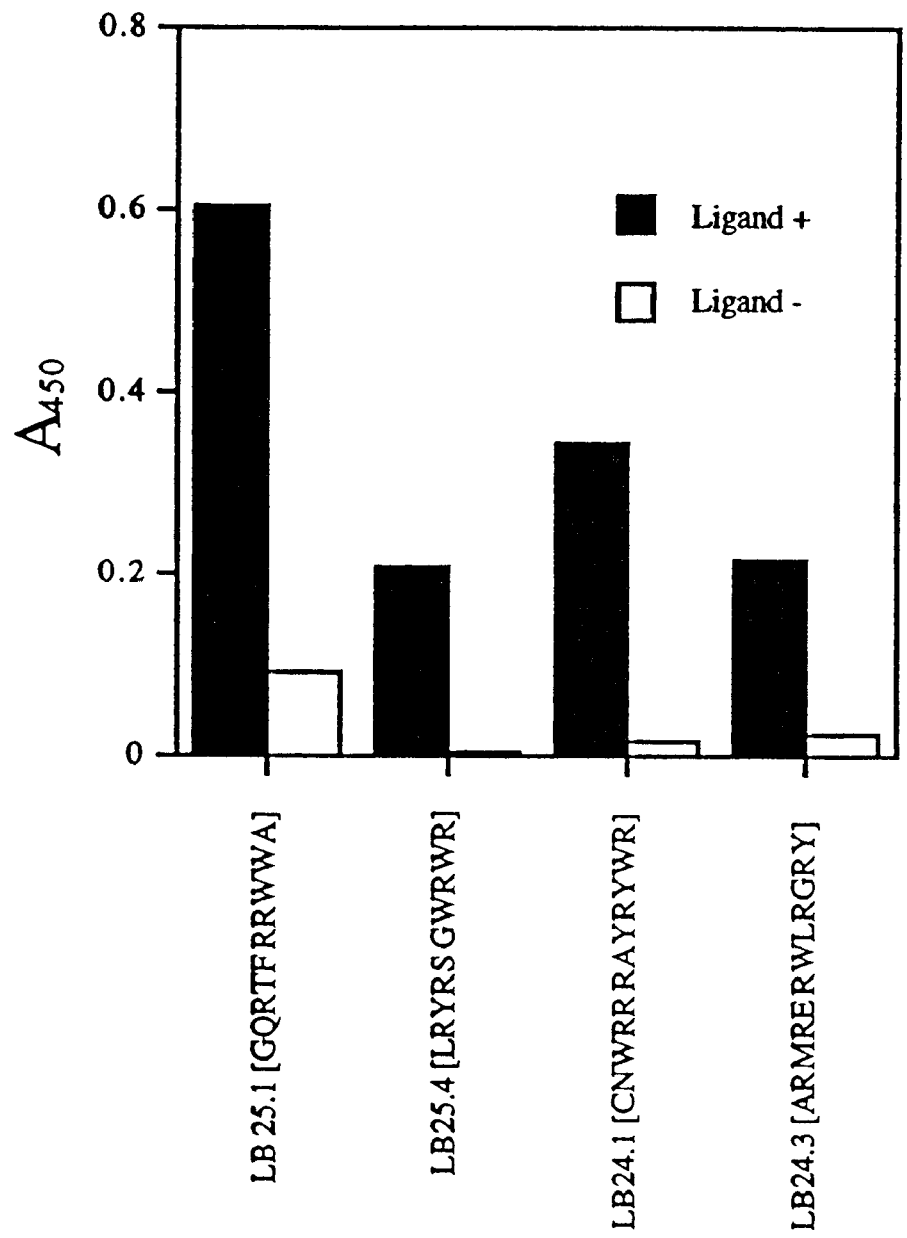
FIG. 12. (Fluorescein-1) Phage ELISA of four clones, pLB25.1 (containing SEQ ID NO:115), pLB25.4 (containing SEQ ID NO:116), pLB24.1 (containing SEQ ID NO:117) and pLB24.3 (containing SEQ ID NO:118). Experimental conditions are the same as ubiquitin-1 above.

The 2D NOESY spectrum of D1.34 provided further evidence for a preserved conformation. The region in the spectrum showed interactions between upfield methyl protons (<0.5 ppm) and methyl-methylene protons. The Val72 γ methyl resonances were well separated in the wild-type spectrum (−0.07 and 0.37 ppm; (Baron et al., 1992)). Resonances corresponding to the two methyl protons are present in the D1.3-4 spectrum (−0.07 and 0.44 ppm). The cross peak between these two resonances and other conserved cross peaks indicate that the two resonances in the D1.3-4 spectrum are highly likely those of Val72 and that other methyl protons are in nearly identical environment to that of wild-type Fn3. Minor differences between the two spectra are presumably due to small structural perturbation due to the mutations. Val72 is on the F strand, where it forms a part of the central hydrophobic core of Fn3 (Main et al., 1992). It is only four residues away from the mutated residues of the FG loop (Table 1). The results are remarkable because, despite there being 7 mutations and 3 deletions in the loop (more than 10% of total residues; FIG. 12, Table 2), D1.3-4 retains a 3D structure virtually identical to that of the wild-type (except for the mutated loop). Therefore, the results provide strong support that the FG loop is not significantly contributing to the folding and stability of the Fn3 molecule and thus that the FG loop can be mutated extensively.

mately 79° C. for the wild-type protein. The results indicated that the extensive mutations at the two surface loops did not drastically decrease the stability of Fn3, and thus demonstrated the feasibility of introducing a large number of mutations in both loops.

Stability was also determined by guanidinium chloride (GdnCl)- and urea-induced unfolding reactions. Preliminary unfolding curves were recorded using a fluorometer equipped with a motor-driven syringe; GdnCl or urea were added continuously to the protein solution in the cuvette. Based on the preliminary unfolding curves, separate samples

TABLE 2

Sequences of oligonucleotides

| Name | Sequence | |
|---|---|---|
| FN1F | CGGGATCCCATATGCAGGTTTCTGATGTTCCGCGTGACCTGGAAGTTGTTGCTGCGACC | (SEQ ID NO: 13) |
| FN1R | TAACTGCAGGAGCATCCCAGCTGATCAGCAGGCTAGTCGGGGTCGCAGCAACAAC | (SEQ ID NO: 14) |
| FN2F | CTCCTGCAGTTACCGTGCGTTATTACCGTATCACGTACGGTGAAACCGGTG | (SEQ ID NO: 15) |
| FN2R | GTGAATTCCTGAACCGGGGAGTTACCACCGGTTTCACCG | (SEQ ID NO: 16) |
| FN3F | AGGAATTCACTGTACCTGGTTCCAAGTCTACTGCTACCATCAGCGG | (SEQ ID NO: 17) |
| FN3R | GTATAGTCGACACCCGGTTTCAGGCCGCTGATGGTAGC | (SEQ ID NO: 18) |
| FN4F | CGGGTGTCGACTATACCATCACTGTATACGCT | (SEQ ID NO: 19) |
| FN4R | CGGGATCCGAGCTCGCTGGGCTGTCACCACGGCCAGTAACAGCGTATACAGTGAT | (SEQ ID NO: 20) |
| FN5F | CAGCGAGCTCCAAGCCAATCTCGATTAACTACCGT | (SEQ ID NO: 21) |
| FN5R | CGGGATCCTCGAGTTACTAGGTACGGTAGTTAATCGA | (SEQ ID NO: 22) |
| FN5R' | CGGGATCCACGCGTGCCACCGGTACGGTAGTTAATCGA | (SEQ ID NO: 23) |
| gene3F | CGGGATCCACGCGTCCATTCGTTTGTGAATATCAAGGCCAATCG | (SEQ ID NO: 24) |
| gene3R | CCGGAAGCTTTAAGACTCCTTATTACGCAGTATGTTAGC | (SEQ ID NO: 25) |
| 38TAABg1II | CTGTTACTGGCCGTGAGATCTAACCAGCGAGCTCCA | (SEQ ID NO: 26) |
| BC3 | GATCAGCTGGGATGCTCCTNNKNNNKNNKNNKNNKTATTACCGTATCACGTA | (SEQ ID NO: 27) |
| FG2 | TGTATACGCTGTTACTGGCNNKNNKNNKNNKNNKNNKNNKTCCAAGCCAATCTCGAT | (SEQ ID NO: 28) |
| FG3 | CTGTATACGCTGTTACTGGCNNKNNKNNKNNKCCAGCGAGCTCCAAG | (SEQ ID NO: 29) |
| FG4 | CATCACTGTATACGCTGTTACTNNKNNKNNKNNKNNKNNKTCCAAGCCAATCTC | (SEQ ID NO: 30) |

Restriction enzyme sites are underlined.
N and K denote an equimolar mixture of A, T, G and C and that of G and T, respectively.

Structure and Stability Measurements

Structures of Abs were analyzed using quantitative methods (e.g., DSSP (Kabsch & Sander, 1983) and PDBFIT (D. McRee, The Scripps Research Institute)) as well as computer graphics (e.g., QUANTA (Molecular Simulations) and WHAT IF (G. Vriend, European Molecular Biology Laboratory)) to superimpose the strand-loop-strand structures of Abs and Fn3.

The stability of FnAbs was determined by measuring temperature- and chemical denaturant-induced unfolding reactions (Pace et al., 1989). The temperature-induced unfolding reaction was measured using a circular dichroism (CD) polarimeter. Ellipticity at 222 and 215 nm was recorded as the sample temperature was slowly raised. Sample concentrations between 10 and 50 $\mu$M were used. After the unfolding baseline was established, the temperature was lowered to examine the reversibility of the unfolding reaction. Free energy of unfolding was determined by fitting data to the equation for the two-state transition (Becktel & Schellman, 1987; Pace et al., 1989). Nonlinear least-squares fitting was performed using the program IGOR (WaveMetrics) on a Macintosh computer.

The structure and stability of two selected mutant Fn3s were studied; the first mutant was D1.34 (Table 2) and the second was a mutant called AS40 which contains four mutations in the BC loop ($A^{26}V^{27}T^{28}V^{29}$)→TQRQ). AS40 was randomly chosen from the BC loop library described above. Both mutants were expressed as soluble proteins in E. coli and were concentrated at least to 1 mM, permitting NMR studies.

The mid-point of the thermal denaturation for both mutants was approximately 69° C., as compared to approxicontaining varying concentration of a denaturant were prepared and fluorescence (excitation at 290 nm, emission at 300–400 nm) or CD (ellipticity at 222 and 215 nm) were measured after the samples were equilibrated at the measurement temperature for at least one hour. The curve was fitted by the least-squares method to the equation for the two-state model (Santoro & Bolen, 1988; Koide et al., 1993). The change in protein concentration was compensated if required.

Once the reversibility of the thermal unfolding reaction is established, the unfolding reaction is measured by a Microcal MC-2 differential scanning calorimeter (DSC). The cell (~1.3 ml) will be filled with FnAb solution (0.1–1 mM) and $\Delta Cp$ (=$\Delta H/\Delta T$) will be recorded as the temperature is slowly raised. $T_m$ (the midpoint of unfolding), $\Delta H$ of unfolding and $\Delta G$ of unfolding is determined by fitting the transition curve (Privalov & Potekhin, 1986) with the ORIGIN software provided by Microcal.

Thermal Unfolding

Figure 3B:
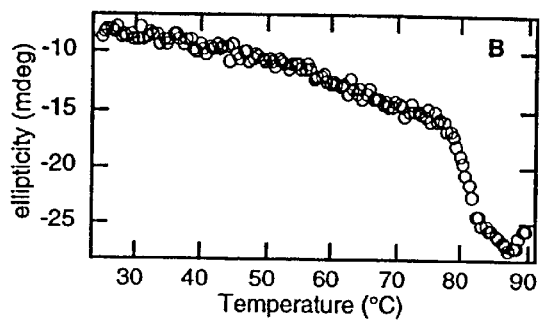
FIG. 3B. Thermal denaturation of Fn3 monitored at 215 nm. Temperature was increased at a rate of 1° C./min.

A temperature-induced unfolding experiment on Fn3 was performed using circular dichroism (CD) spectroscopy to monitor changes in secondary structure. The CD spectrum of the native Fn3 shows a weak signal near 222 nm (FIG. 3A), consistent with the predominantly β-structure of Fn3 (Perczel et al., 1992). A cooperative unfolding transition is observed at 80–90° C., clearly indicating high stability of Fn3 (FIG. 3B). The free energy of unfolding could not be determined due to the lack of a post-transition baseline. The result is consistent with the high stability of the first Fn3 domain of human fibronectin (Litvinovich et al., 1992), thus indicating that Fn3 domains are in general highly stable.

Binding Assays

Binding reaction of FnAbs were characterized quantitatively using an isothermal titration calorimeter (ITC) and fluorescence spectroscopy.

The enthalpy change (ΔH) of binding were measured using a Microcal OMEGA ITC (Wiseman et al., 1989). The sample cell (~1.3 ml) was filled with FnAbs solution (≦100 μM, changed according to $K_d$), and the reference cell filled with distilled water; the system was equilibrated at a given temperature until a stable baseline is obtained; 5–20 μl of ligand solution (≦2 mM) was injected by a motordriven syringe within a short duration (20 sec) followed by an equilibration delay (4 minutes); the injection was repeated and heat generation/absorption for each injection was measured. From the change in the observed heat change as a function of ligand concentration, ΔH and $K_d$ was determined (Wiseman et al., 1989). ΔG and ΔS of the binding reaction was deduced from the two directly measured parameters. Deviation from the theoretical curve was examined to assess nonspecific (multiplesite) binding. Experiments were also performed by placing a ligand in the cell and titrating with an FnAb. It should be emphasized that only ITC gives direct measurement of ΔH, thereby making it possible to evaluate enthalpic and entropic contributions to the binding energy. ITC was successfully used to monitor the binding reaction of the D1.3 Ab (Tello et al., 1993; Bhat et al., 1994).

Intrinsic fluorescence is monitored to measure binding reactions with $K_d$ in the sub-μM range where the determination of $K_d$ by ITC is difficult. Trp fluorescence (excitation at ~290 nm, emission at 300–350 nm) and Tyr fluorescence (excitation at ~260 nm, emission at ~303 nm) is monitored as the Fn3-mutant solution (≦10 μM) is titrated with ligand solution (≦100 μM). $K_d$ of the reaction is determined by the nonlinear least-squares fitting of the bimolecular binding equation. Presence of secondary binding sites is examined using Scatchard analysis. In all binding assays, control experiments are performed busing wild-type Fn3 (or unrelated FnAbs) in place of FnAbs of interest.

II. Production of Fn3 Mutants with High Affinity and Specificity FnAbs

Library screening was carried out in order to select FnAbs which bind to specific ligands. This is complementary to the modeling approach described above. The advantage of combinatorial screening is that one can easily produce and screen a large number of variants ($\geq 10^8$), which is not feasible with specific mutagenesis ("rational design") approaches. The phage display technique (Smith, 1985; O'Neil & Hoess, 1995) was used to effect the screening processes. Fn3 was fused to a phage coat protein (pHI) and displayed on the surface of filamentous phages. These phages harbor a single-stranded DNA genome that contains the gene coding the Fn3 fusion protein. The amino acid sequence of defined regions of Fn3 were randomized using a degenerate nucleotide sequence, thereby constructing a library. Phages displaying Fn3 mutants with desired binding capabilities were selected in vitro, recovered and amplified. The amino acid sequence of a selected clone can be identified readily by sequencing the Fn3 gene of the selected phage. The protocols of Smith (Smith & Scott, 1993) were followed with minor modifications.

The objective was to produce FnAbs which have high affinity to small protein ligands. HEL and the B1 domain of staphylococcal protein G (hereafter referred to as protein G) were used as ligands. Protein G is small (56 amino acids) and highly stable (Minor & Kim, 1994; Smith et al., 1994). Its structure was determined by NMR spectroscopy (Gronenbom et al., 1991) to be a helix packed against a four-strand β-sheet. The resulting FnAb-protein G complexes (~150 residues) is one of the smallest protein-protein complexes produced to date, well within the range of direct NMR methods. The small size, the high stability and solubility of both components and the ability to label each with stable isotopes ($^{13}C$ and $^{15}N$; see below for protein G) make the complexes an ideal model system for NMR studies on protein-protein interactions.

The successful loop replacement of Fn3 (the mutant D1.34) demonstrate that at least ten residues can be mutated without the loss of the global fold. Based on this, a library was first constructed in which only residues in the FG loop are randomized. After results of loop replacement experiments on the BC loop were obtained, mutation sites were extended that include the BC loop and other sites.

Construction of Fn3 Phase Display System

An M13 phage-based expression vector pASM1 has been constructed as follows: an oligonucleotide coding the signal peptide of OmpT was cloned at the 5' end of the Fn3 gene; a gene fragment coding the C-terminal domain of M13 pIII was prepared from the wild-type gene III gene of M13 mp18 using PCR (Corey et al., 1993) and the fragment was inserted at the 3' end of the OmpT-Fn3 gene; a spacer sequence has been inserted between Fn3 and pIII. The resultant fragment (OmpTFn3-pIII) was cloned in the multiple cloning site of M13 mp18, where the fusion gene is under the control of the lac promoter. This system will produce the Fn3-pIII fusion protein as well as the wild-type pIII protein. The co-expression of wild-type pIII is expected to reduce the number of fusion pIII protein, thereby increasing the phage infectivity (Corey et al., 1993) (five copies of pIII are present on a phage particle). In addition, a smaller number of fusion pIII protein may be advantageous in selecting tight binding proteins, because the chelating effect due to multiple binding sites should be smaller than that with all five copies of fusion pIII (Bass et al., 1990). This system has successfully displayed the serine protease trypsin (Corey et al., 1993). Phages were produced and purified using *E. coli* K91 kan (Smith & Scott, 1993) according to a standard method (Sambrook et al., 1989) except that phage particles were purified by a second polyethylene glycol precipitation and acid precipitation.

Successful display of Fn3 on fusion phages has been confirmed by ELISA using an Ab against fibronectin (Sigma), clearly indicating that it is feasible to construct libraries using this system.

An alternative system using the fUSE5 (Parmley & Smith, 1988) may also be used. The Fn3 gene is inserted to fUSE5 using the SfiI restriction sites introduced at the 5'- and 3'- ends of the Fn3 gene PCR. This system displays only the fusion pIII protein (up to five copies) on the surface of a phage. Phages are produced and purified as described (Smith & Scott, 1993). This system has been used to display many proteins and is robust. The advantage of fUSE5 is its low toxicity. This is due to the low copy number of the replication form (RF) in the host, which in turn makes it difficult to prepare a sufficient amount of RF for library construction (Smith & Scott, 1993).

Construction of Libraries

The first library was constructed of the Fn3 domain displayed on the surface of MB phage in which seven residues (77–83) in the FG loop (FIG. 4D) were randomized. Randomization will be achieved by the use of an oligonucleotide containing degenerated nucleotide sequence. A double-stranded nucleotide was prepared by the same protocol as for gene synthesis (see above) except that one strand had an $(NNK)_6(NNG)$ sequence at the mutation sites, where N corresponds to an equimolar mixture of A, T, G and C and K corresponds to an equimolar mixture of G and T. The (NNG) codon at residue 83 was required to conserve the SacI restriction site (FIG. 2). The (NNK) codon codes all of the 20 amino acids, while the NNG codon codes 14. Therefore, this library contained ~$10^9$ independent sequences. The library was constructed by ligating the double-stranded nucleotide into the wild-type phage vector, pASM 1, and the transfecting E. coli XL1 blue (Stratagene) using electroporation. XL1 blue has the lacI$^q$ phenotype and thus suppresses the expression of the Fn3-pIII fusion protein in the absence of lac inducers. The initial library was propagated in this way, to avoid selection against toxic Fn3-pIII clones. Phages displaying the randomized Fn3-pIII fusion protein were prepared by propagating phages with K91 kan as the host. K91 kan does not suppress the production of the fusion protein, because it does not have lacI$^q$. Another library was also generated in which the BC loop (residues 26–20) was randomized.

Selection of Displayed FnAbs

Screening of Fn3 phage libraries was performed using the biopanning protocol (Smith & Scott, 1993); a ligand is biotinylated and the strong biotinstreptavidin interaction was used to immobilize the ligand on a streptavidin-coated dish. Experiments were performed at room temperature (~22° C.). For the initial recovery of phages from a library, 10 μg of a biotinylated ligand were immobilized on a streptavidin-coated polystyrene dish (35 mm, Falcon 1008) and then a phage solution (containing ~$10^{11}$ pfu (plaque-forming unit)) was added. After washing the dish with an appropriate buffer (typically TBST, Tris-HCl (50 mM, pH 7.5), NaCl (150 mM) and Tween 20 (0.5%)), bound phages were eluted by one or combinations of the following conditions: low pH, an addition of a free ligand, urea (up to 6 M) and, in the case of anti-protein G FnAbs, cleaving the protein G-biotin linker by thrombin. Recovered phages were amplified using the standard protocol using K91 kan as the host (Sambrook et al., 1989). The selection process were repeated 3–5 times to concentrate positive clones. From the second round on, the amount of the ligand were gradually decreased (to ~1 μg) and the biotinylated ligand were mixed with a phage solution before transferring a dish (G. P. Smith, personal communication). After the final round, 10–20 clones were picked, and their DNA sequence will be determined. The ligand affinity of the clones were measured first by the phage-ELISA method (see below).

To suppress potential binding of the Fn3 framework (background binding) to a ligand, wild-type Fn3 may be added as a competitor in the buffers. In addition, unrelated proteins (e.g., bovine serum albumin, cytochrome c and RNase A) may be used as competitors to select highly specific FnAbs.

Binding Assay

The binding affinity of FnAbs on phage surface is characterized semiquantitatively using the phage ELISA technique (Li et al., 1995). Wells of microtiter plates (Nunc) are coated with a ligand protein (or with streptavidin followed by the binding of a biotinylated ligand) and blocked with the BLOTTO solution (Pierce). Purified phages (~$10^{10}$ pfu) originating from single plaques (M13)/colonies (fUSE5) are added to each well and incubated overnight at 4° C. After washing wells with an appropriate buffer (see above), bound phages are detected by the standard ELISA protocol using anti-M13 Ab (rabbit, Sigma) and anti-rabbit Ig-peroxidase conjugate (Pierce) or using anti-M13 Ab-peroxidase conjugate (Pharmacia). Colormetric assays are performed using TMB (3,3',5,5'-tetramethylbenzidine, Pierce). The high affinity of protein G to immunoglobulins present a special problem; Abs cannot be used in detection. Therefore, to detect anti-protein G FnAbs, fusion phages are immobilized in wells and the binding is then measured using biotinylated protein G followed by the detection using streptavidin-peroxidase conjugate.

Production of Soluble FnAbs

After preliminary characterization of mutant Fn3s using phage ELISA, mutant genes are subcloned into the expression vector pEW1. Mutant proteins are produced as His•tag fusion proteins and purified, and their conformation, stability and ligand affinity are characterized.

Thus, Fn3 is the fourth example of a monomeric immunoglobulin-like scaffold that can be used for engineering binding proteins. Successful selection of novel binding proteins have also been based on minibody, tendamistat and "camelized" immunoglobulin VH domain scaffolds (Martin et al., 1994; Davies & Riechmann, 1995; McConnell & Hoess, 1995). The Fn3 scaffold has advantages over these systems. Bianchi et al. reported that the stability of a minibody was 2.5 kcal/mol, significantly lower than that of Ubi4-K. No detailed structural characterization of minibodies has been reported to date. Tendamistat and the VH domain contain disulfide bonds, and thus preparation of correctly folded proteins may be difficult. Davies and Riechmann reported that the yields of their camelized VH domains were less than 1 mg per liter culture (Davies & Riechmann, 1996).

Thus, the Fn3 framework can be used as a scaffold for molecular recognition. Its small size, stability and well-characterized structure make Fn3 an attractive system. In light of the ubiquitous presence of Fn3 in a wide variety of natural proteins involved in ligand binding, one can engineer Fn3-based binding proteins to different classes of targets.

The following examples are intended to illustrate but not limit the invention.

EXAMPLE I

Construction of the Fn3 Gene

A synthetic gene for tenth Fn3 of fibronectin (FIG. 1) was designed on the basis of amino acid residue 1416–1509 of human fibronectin (Kornblihtt, et al., 1985) and its three dimensional structure (Main, et al., 1992). The gene was engineered to include convenient restriction sites for mutagenesis and the so-called "preferred codons" for high level protein expression (Gribskov, et al., 1984) were used. In addition, a glutamine residue was inserted after the N-terminal methionine in order to avoid partial processing of the N-terminal methionine which often degrades NMR spectra (Smith, et al., 1994). Chemical reagents were of the analytical grade or better and purchased from Sigma Chemical Company and J. T. Baker, unless otherwise noted. Recombinant DNA procedures were performed as described in "Molecular Cloning" (Sambrook, et al., 1989), unless otherwise stated. Custom oligonucleotides were purchased from Operon Technologies. Restriction and modification enzymes were from New England Biolabs.

The gene was assembled in the following manner. First, the gene sequence (FIG. 5) was divided into five parts with boundaries at designed restriction sites: fragment 1, NdeI-PstI (oligonucleotides FN 1F and FN1R (Table 2); fragment 2, PstI-EcoRI (FN2F and FN2R); fragment 3, EcoRI-SalI (FN3F and FN3R); fragment 4, SalI-SacI (FN4F and FN4R); fragment 5, SacI-BamHI (FN5F and FN5R). Second, for each part, a pair of oligonucleotides which code opposite strands and have complementary overlaps of approximately 15 bases was synthesized. These oligonucleotides were designated FN1F–FN5R and are shown in Table 2. Third, each pair (e.g., FN1F and FN1R) was annealed and single-strand regions were filled in using the Klenow fragment of DNA polymerase. Fourth, the double stranded oligonucleotide was digested with the relevant restriction enzymes at the termini of the fragment and cloned into the PBLUESCRIPT SK plasmid (Stratagene) which had been digested with the same enzymes as those used for the fragments. The DNA sequence of the inserted fragment was confirmed by DNA sequencing using an Applied Biosystems DNA sequencer and the dideoxy termination protocol provided by the manufacturer. Last, steps 2–4 were repeated to obtain the entire gene.

Figure 6:
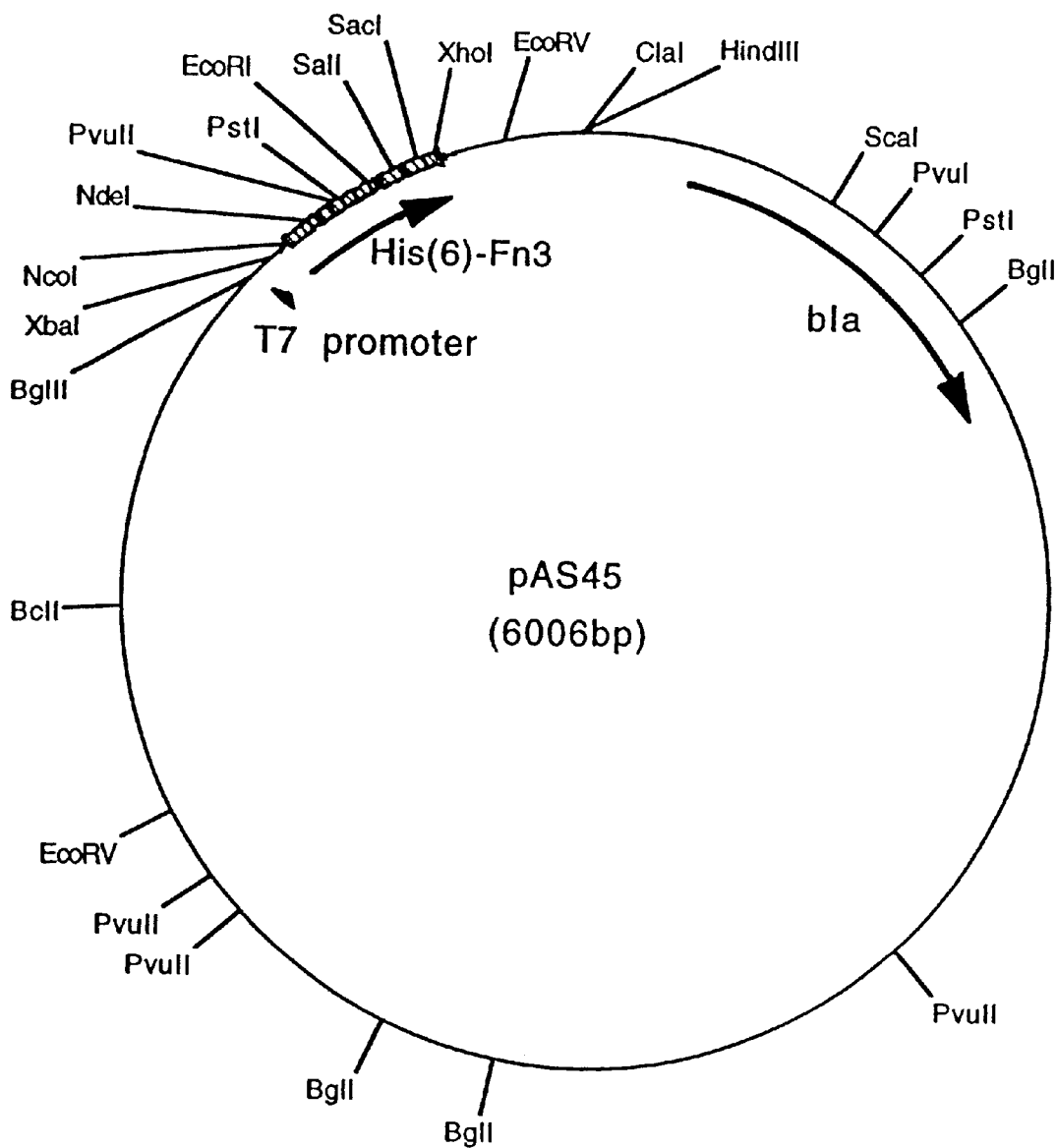
FIG. 6. Map of plasmid pAS45. Plasmid pAS45 is the expression vector of His•tag-Fn3.

The gene was also cloned into the pET3a and pETI 5b (Novagen) vectors (pAS45 and pAS25, respectively). The maps of the plasmids are shown in FIGS. 6 and 7. $E.\ coli$ BL21 (DE3) (Novagen) containing these vectors expressed the Fn3 gene under the control of bacteriophage T7 promotor (Studier, et al., 1990); pAS24 expresses the 96-residue Fn3 protein only, while pAS45 expresses Fn3 as a fusion protein with poly-histidine peptide (His•tag). High level expression of the Fn3 protein and its derivatives in $E.\ coli$ was detected as an intense band on SDS-PAGE stained with CBB.

The binding reaction of the monobodies is characterized quantitatively by means of fluorescence spectroscopy using purified soluble monobodies.

Intrinsic fluorescence is monitored to measure binding reactions. Trp fluorescence (excitation at ~290 nm, emission at 300 350 nm) and Tyr fluorescence (excitation at ~260 nm, emission at 303 nm) is monitored as the Fn3-mutant solution ($\leq 100\ \mu M$) is titrated with a ligand solution. When a ligand is fluorescent (e.g. fluorescein), fluorescence from the ligand may be used. $K_d$ of the reaction will be determined by the nonlinear least-squares fitting of the bimolecular binding equation.

If intrinsic fluorescence cannot be used to monitor the binding reaction, monobodies are labeled with fluorescein-NHS (Pierce) and fluorescence polarization is used to monitor the binding reaction (Burke et al., 1996).

EXAMPLE II

Modifications to Include Restriction Sites in the Fn3 Gene

The restriction sites were incorporated in the synthetic Fn3 gene without changing the amino acid sequence Fn3. The positions of the restriction sites were chosen so that the gene construction could be completed without synthesizing long (>60 bases) oligonucleotides and so that two loop regions could be mutated (including by randomization) by the cassette mutagenesis method (i.e., swapping a fragment with another synthetic fragment containing mutations). In addition, the restriction sites were chosen so that most sites were unique in the vector for phage display. Unique restriction sites allow one to recombine monobody clones which have been already selected in order to supply a larger sequence space.

EXAMPLE III

Construction of M13 Phage Display Libraries

Figure 8:
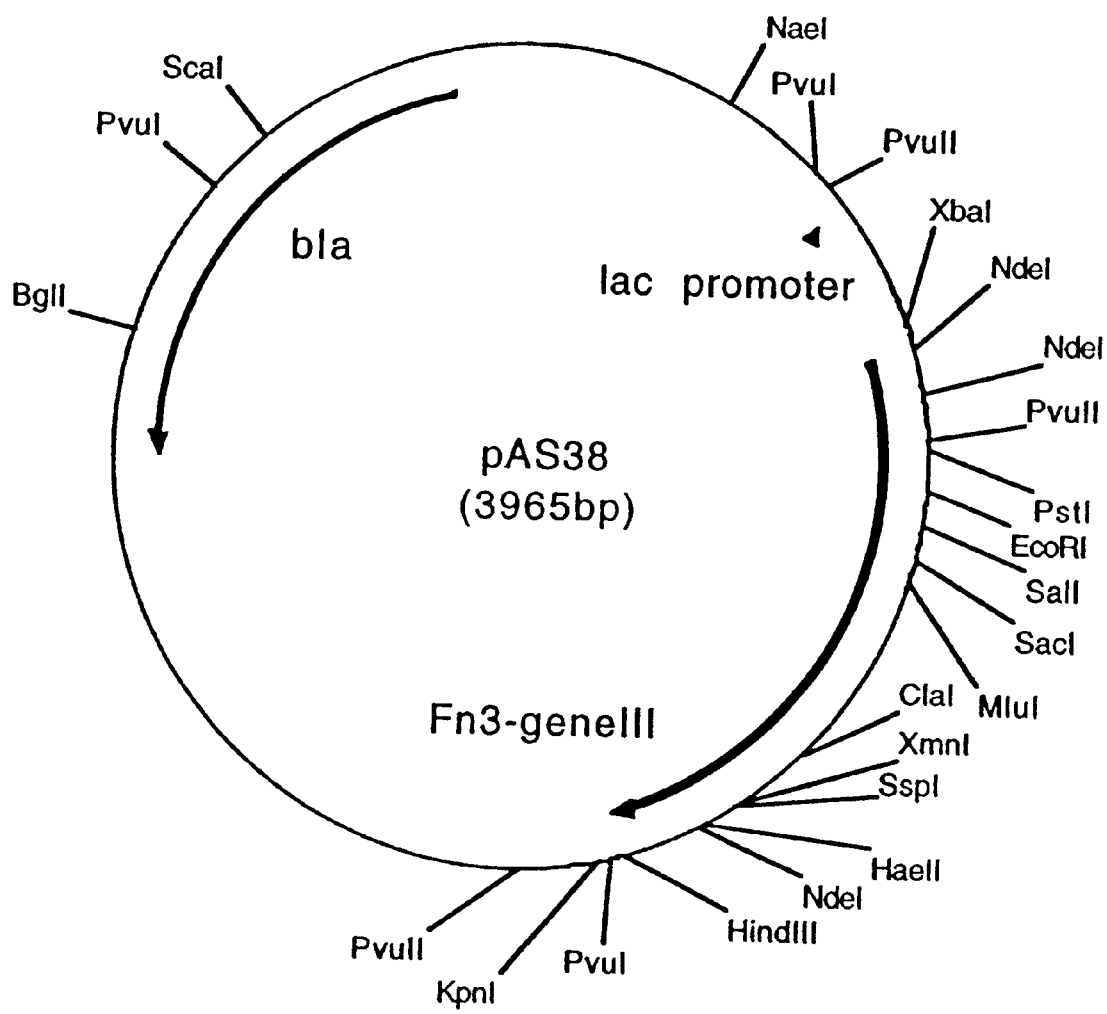
FIG. 8. Map of plasmid pAS38. pAS38 is a phagmid vector for the surface display of Fn3.

A vector for phage display, pAS38 (for its map, see FIG. 8) was constructed as follows. The XbaI-BamHI fragment of pET12a encoding the signal peptide of OmpT was cloned at the 5' end of the Fn3 gene. The C-terminal region (from the FN5F and FN5R' oligonucleotides, see Table 2) of the Fn3 gene was replaced with a new fragment consisting of the FN5F and FN5R' oligonucleotides (Table 2) which introduced a MluI site and a linker sequence for making a fusion protein with the pIII protein of bacteriophage M13. A gene fragment coding the C-terminal domain of M13 pIII was prepared from the wild-type gene III of M13mp18 using PCR (Corey, et al., 1993) and the fragment was inserted at the 3' end of the OmpT-Fn3 fusion gene using the MluI and HindIII sites.

Phages were produced and purified using a helper phage, M13K07, according to a standard method (Sambrook, et al., 1989) except that phage particles were purified by a second polyethylene glycol precipitation. Successful display of Fn3 on fusion phages was confirmed by ELISA (Harlow & Lane, 1988) using an antibody against fibronectin (Sigma) and a custom anti-FN3 antibody (Cocalico Biologicals, PA, USA).

EXAMPLE IV

Libraries Containing Loop Variegations in the AB Loop

A nucleic acid phage display library having variegation in the AB loop is prepared by the following methods. Randomization is achieved by the use of oligonucleotides containing degenerated nucleotide sequence. Residues to be variegated are identified by examining the X-ray and NMR structures of Fn3 (Protein Data Bank accession numbers, 1FNA and 1TTF, respectively). Oligonucleotides containing NNK (N and K here denote an equimolar mixture of A, T, G, and C and an equimolar mixture of G and T, respectively) for the variegated residues are synthesized (see oligonucleotides BC3, FG2, FG3, and FG4 in Table 2 for example). The NNK mixture codes for all twenty amino acids and one termination codon (TAG). TAG, however, is suppressed in the $E.\ coli$ XL-1 blue. Single-stranded DNAs of pAS38 (and its derivatives) are prepared using a standard protocol (Sambrook, et al., 1989).

Site-directed mutagenesis is performed following published methods (see for example, Kunkel, 1985) using a MUTA-GENE kit (BioRad). The libraries are constructed by electroporation of $E.\ coli$ XL-1 Blue electroporation competent cells (200 $\mu l$; Stratagene) with 1 $\mu g$ of the plasmid DNA using a BTX electrocell manipulator ECM 395 1 mm gap cuvette. A portion of the transformed cells is plated on an LB-agar plate containing ampicillin (100 $\mu g/ml$) to determine the transformation efficiency. Typically, $3 \times 10^8$ transformants are obtained with 1 $\mu g$ of DNA, and thus a library contains $10^8$ to $10^9$ independent clones. Phagemid particles were prepared as described above.

EXAMPLE V

Loop variegations in the BC, CD, DE, EF or FG Loop

A nucleic acid phage display library having five variegated residues (residues number 26–30) in the BC loop, and one having seven variegated residues (residue numbers 78–84) in the FG loop, was prepared using the methods described in Example IV above. Other nucleic acid phage display libraries having variegation in the CD, DE or EF loop can be prepared by similar methods.

EXAMPLE VI

Loop Variegations in the FG and BC Loop

A nucleic acid phage display library having seven variegated residues (residues number 78–84) in the FG loop and five variegated residues (residue number 26–30) in the BC loop was prepared. Variegations in the BC loop were prepared by site-directed mutagenesis (Kunkel, et al.) using the BC3 oligonucleotide described in Table 1. Variegations in the FG loop were introduced using site-directed mutagenesis using the BC loop library as the starting material, thereby resulting in libraries containing variegations in both BC and FG loops. The oligonucleotide FG2 has variegating residues 78–84 and oligonucleotide FG4 has variegating residues 77–81 and a deletion of residues 82–84.

A nucleic acid phage display library having five variegated residues (residues 78–84) in the FG loop and a three residue deletion (residues 82–84) in the FG loop, and five variegated residues (residues 26–30) in the BC loop, was prepared. The shorter FG loop was made in an attempt to reduce the flexibility of the FG loop; the loop was shown to be highly flexible in Fn3 by the NMR studies of Main, et al. (1992). A highly flexible loop may be disadvantageous to forming a binding site with a high affinity (a large entropy loss is expected upon the ligand binding, because the flexible loop should become more rigid). In addition, other Fn3 domains (besides human) have shorter FG loops (for sequence alignment, see FIG. 12 in Dickinson, et al. (1994)).

Randomization was achieved by the use of oligonucleotides containing degenerate nucleotide sequence (oligonucleotide BC3 for variegating the BC loop and oligonucleotides FG2 and FG4 for variegating the FG loops).

Site-directed mutagenesis was performed following published methods (see for example, Kunkel, 1985). The libraries were constructed by electrotransforming E. coli XL-1 Blue (Stratagene). Typically a library contains $10^8$ to $10^9$ independent clones. Library 2 contains five variegated residues in the BC loop and seven variegated residues in the FG loop. Library 4 contains five variegated residues in each of the BC and FG loops, and the length of the FG loop was shortened by three residues.

EXAMPLE VII fd Phage Display Libraries Constructed with Loop Variegations

Phage display libraries are constructed using the fd phage as the genetic vector. The Fn3 gene is inserted in fUSE5 (Parmley & Smith, 1988) using SfiI restriction sites which are introduced at the 5' and 3' ends of the Fn3 gene using PCR. The expression of this phage results in the display of the fusion pIII protein on the surface of the fd phage. Variegations in the Fn3 loops are introduced using site-directed mutagenesis as described hereinabove, or by subcloning the Fn3 libraries constructed in M13 phage into the fuSE5 vector.

EXAMPLE VIII

Other Phage Display Libraries

T7 phage libraries (Novagen, Madison, Wis.) and bacterial pili expression systems (Invitrogen) are also useful to express the Fn3 gene.

EXAMPLE IX

Isolation of Polypeptides which Bind to Macromolecular Structures

The selection of phage-displayed monobodies was performed following the protocols of Barbas and coworkers (Rosenblum & Barbas, 1995). Briefly, approximately 1 µg of a target molecule ("antigen") in sodium carbonate buffer (100 mM, pH 8.5) was immobilized in the wells of a microtiter plate (Maxisorp, Nunc) by incubating overnight at 4° C. in an air tight container. After the removal of this solution, the wells were then blocked with a 3% solution of BSA (Sigma, Fraction V) in TBS by incubating the plate at 37° C. for 1 hour. A phagemid library solution (50 µl) containing approximately $10^{12}$ colony forming units (cfu) of phagemid was absorbed in each well at 37° C. for 1 hour. The wells were then washed with an appropriate buffer (typically TBST, 50 mM Tris-HCl (pH 7.5), 150 mM NaCl, and 0.5% Tween20) three times (once for the first round). Bound phage were eluted by an acidic solution (typically, 0.1 M glycine-HCl, pH 2.2; 50 µl) and recovered phage were immediately neutralized with 3 µl of Tris solution. Alternatively, bound phage were eluted by incubating the wells with 50 µl of TBS containing the antigen (1–10 µM). Recovered phage were amplified using the standard protocol employing the XL1 Blue cells as the host (Sambrook, et al.). The selection process was repeated 5–6 times to concentrate positive clones. After the final round, individual clones were picked and their binding affinities and DNA sequences were determined.

The binding affinities of monobodies on the phage surface were characterized using the phage ELISA technique (Li, et al., 1995). Wells of microtiter plates (Nunc) were coated with an antigen and blocked with BSA. Purified phages ($10^8$–$10^{11}$ cfu) originating from a single colony were added to each well and incubated 2 hours at 37° C. After washing wells with an appropriate buffer (see above), bound phage were detected by the standard ELISA protocol using antiM13 antibody (rabbit, Sigma) and anti-rabbit Ig-peroxidase conjugate (Pierce). Colorimetric assays were performed using Turbo-TMB (3,3',5,5'-tetramethylbenzidine, Pierce) as a substrate.

The binding affinities of monobodies on the phage surface were further characterized using the competition ELISA method (Djavadi-Ohaniance, et al., 1996). In this experiment, phage ELISA is performed in the same manner as described above, except that the phage solution contains a ligand at varied concentrations. The phage solution was incubated a 4° C. for one hour prior to the binding of an immobilized ligand in a microtiter plate well. The affinities of phage displayed monobodies are estimated by the decrease in ELISA signal as the free ligand concentration is increased.

After preliminary characterization of monobodies displayed on the surface of phage using phage ELISA, genes for positive clones were subcloned into the expression vector pAS45. E. coli BL21(DE3) (Novagen) was transformed with an expression vector (pAS45 and its derivatives). Cells were grown in M9 minimal medium and M9 medium supplemented with Bactotryptone (Difco) containing ampicillin (200 µg/ml). For isotopic labeling, $^{15}$N NH$_4$Cl and/or $^{13}$C glucose replaced unlabeled components. Stable isotopes were purchased from Isotec and Cambridge Isotope Labs. 500 ml medium in a 2 1 baffle flask was inoculated with 10 ml of overnight culture and agitated at approximately 140 rpm at 37° C. IPTG was added at a final concentration of 1 mM to induce protein expression when OD(600 nm) reached approximately 1.0. The cells were harvested by centrifugation 3 hours after the addition of IPTG and kept frozen at −70° C. until used.

Fn3 and monobodies with His•tag were purified as follows. Cells were suspended in 5 ml/(g cell) of 50 mM Tris (pH 7.6) containing 1 mM phenylmethylsulfonyl fluoride.

HEL (Sigma, 3×crystallized) was added to a final concentration of 0.5 mg/ml. After incubating the solution for 30 min at 37° C., it was sonicated so as to cause cell breakage three times for 30 seconds on ice. Cell debris was removed by centrifugation at 15,000 rpm in an Sorval RC-2B centrifuge using an SS-34 rotor. Concentrated sodium chloride is added to the solution to a final concentration of 0.5 M. The solution was then applied to a 1 ml HISTRAP™ chelating column (Pharmacia) preloaded with nickel chloride (0.1 M, 1 ml) and equilibrated in the Tris buffer (50 mM, pH 8.0) containing 0.5 M sodium chloride. After washing the column with the buffer, the bound protein was eluted with a Tris buffer (50 mM, pH 8.0) containing 0.5 M imidazole. The Hisetag portion was cleaved off, when required, by treating the fusion protein with thrombin using the protocol supplied by Novagen (Madison, Wis). Fn3 was separated from the His•tag peptide and thrombin by a RESOURCES® column (Pharmacia) using a linear gradient of sodium chloride (0–0.5 M) in sodium acetate buffer (20 mM, pH 5.0).

Small amounts of soluble monobodies were prepared as follows. XL-1 Blue cells containing pAS38 derivatives (plasmids coding Fn3-pIII fusion proteins) were grown in LB media at 37° C. with vigorous shaking until OD(600 nm) reached approximately 1.0; IPTG was added to the culture to a final concentration of 1 mM, and the cells were further grown overnight at 37° C. Cells were removed from the medium by centrifugation, and the supernatant was applied to a microtiter well coated with a ligand. Although XL-1 Blue cells containing pAS38 and its derivatives express FN3-pIII fusion proteins, soluble proteins are also produced due to the cleavage of the linker between the Fn3 and pIII regions by proteolytic activities of *E. coli* (Rosenblum & Barbas, 1995). Binding of a monobody to the ligand was examined by the standard ELISA protocol using a custom antibody against Fn3 (purchased from Cocalico Biologicals, Reamstown, Pa.). Soluble monobodies obtained from the periplasmic fraction of *E. coli* cells using a standard osmotic shock method were also used.

EXAMPLE X

Ubiquitin Binding Monobody

Ubiquitin is a small (76 residue) protein involved in the degradation pathway in eurkaryotes. It is a single domain globular protein. Yeast ubiquitin was purchased from Sigma Chemical Company and was used without further purification.

Libraries 2 and 4, described in Example VI above, were used to select ubiquitin-binding monobodies. Ubiquitin (1 μg in 50 μl sodium bicarbonate buffer (100 mM, pH 8.5)) was immobilized in the wells of a microtiter plate, followed by blocking with BSA (3% in TBS). Panning was performed as described above. In the first two rounds, 1 μg of ubiquitin was immobilized per well, and bound phage were elute with an acidic solution. From the third to the sixth rounds, 0.1 μg of ubiquitin was immobilized per well and the phage were eluted either with an acidic solution or with TBS containing 10 μM ubiquitin.

Figure 9:
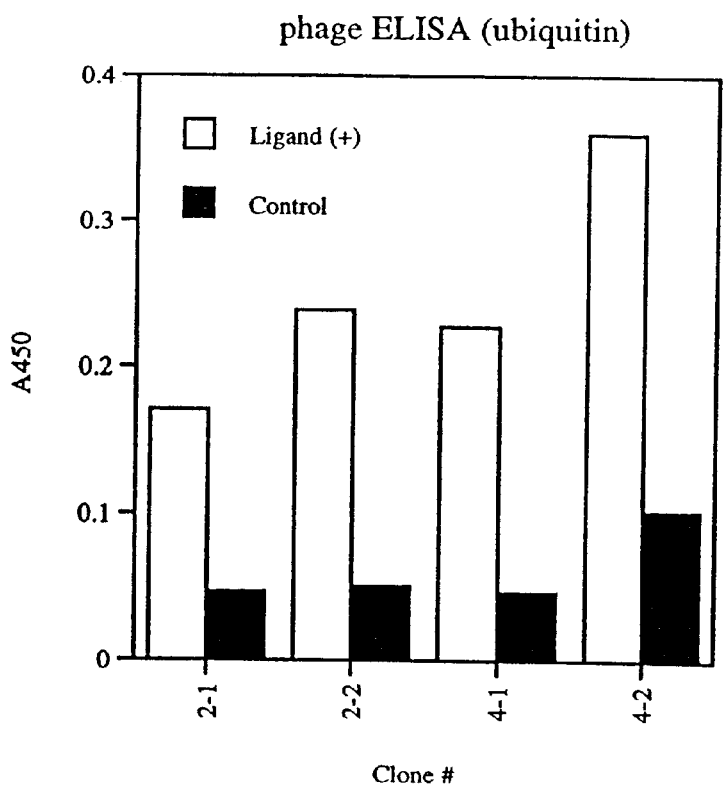
FIG. 9. (Ubiquitin-1) Characterization of ligand-specific binding of enriched clones using phage enzyme-linked immunosolvent assay (ELISA). Microtiter plate wells were coated with ubiquitin (1 μg/well; "Ligand (+)") and then blocked with BSA. Phage solution in TBS containing approximately $10^{10}$ colony forming units (cfu) was added to a well and washed with TBS. Bound phages were detected with anti-phage antibody-POD conjugate (Pharmacia) with Turbo-TMB (Pierce) as a substrate. Absorbance was measured using a Molecular Devices SPECTRAMAX 250 microplate spectrophotometer. For a control, wells without the immobilized ligand were used. 2-1 and 2-2 denote enriched clones from Library 2 eluted with free ligand and acid, respectively. 4-1 and 4-2 denote enriched clones from Library 4 eluted with free ligand and acid, respectively.
Figure 10:
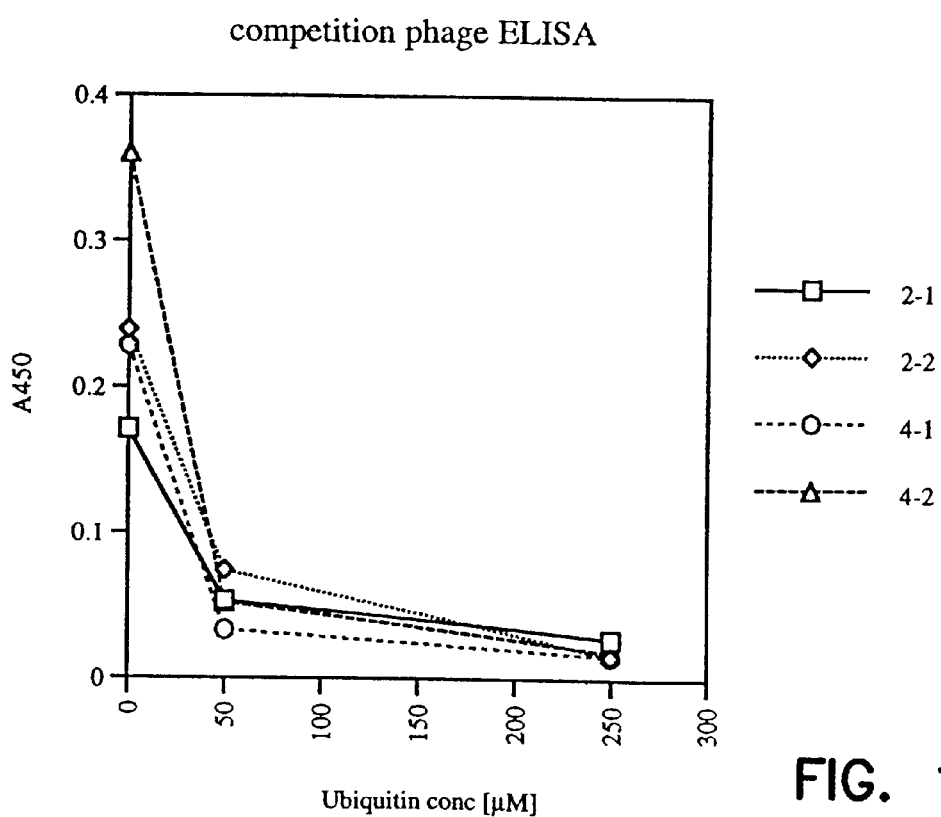
FIG. 10. (Ubiquitin-2) Competition phage ELISA of enriched clones. Phage solutions containing approximately $10^{10}$ cfu were first incubated with free ubiquitin at 4° C. for 1 hour prior to the binding to a ligand-coated well. The wells were washed and phages detected as described above.

Binding of selected clones was tested first in the polyclonal mode, i.e., before isolating individual clones. Selected clones from all libraries showed significant binding to ubiquitin. These results are shown in FIG. 9. The binding to the immobilized ubiquitin of the clones was inhibited almost completely by less than 30 μm soluble ubiquitin in the competition ELISA experiments (see FIG. 10). The sequences of the BC and FG loops of ubiquitin-binding monobodies is shown in Table 3.

TABLE 3

Sequences of ubiquitin-binding monobodies

| Name | BC loop | FG loop | Occurrence (if more than one) |
|---|---|---|---|
| 211 | CARRA (SEQ ID NO:31) | RWIPLAK (SEQ ID NO:32) | 2 |
| 212 | CWRRA (SEQ ID NO:33) | RWVGLAW (SEQ ID NO:34) | |
| 213 | CKHRR (SEQ ID NO:35) | FADLWWR (SEQ ID NO:36) | |
| 214 | CRRGR (SEQ ID NO:37) | RGFMWLS (SEQ ID NO:38) | |
| 215 | CNWRR (SEQ ID NO:39) | RAYRYRW (SEQ ID NO:40) | |
| 411 | SRLRR (SEQ ID NO:41) | PPWRV (SEQ ID NO:42) | 9 |
| 422 | ARWTL (SEQ ID NO:43) | RRWWW (SEQ ID NO:44) | |
| 424 | GQRTF (SEQ ID NO:45) | RRWWA (SEQ ID NO:46) | |

Figure 11:
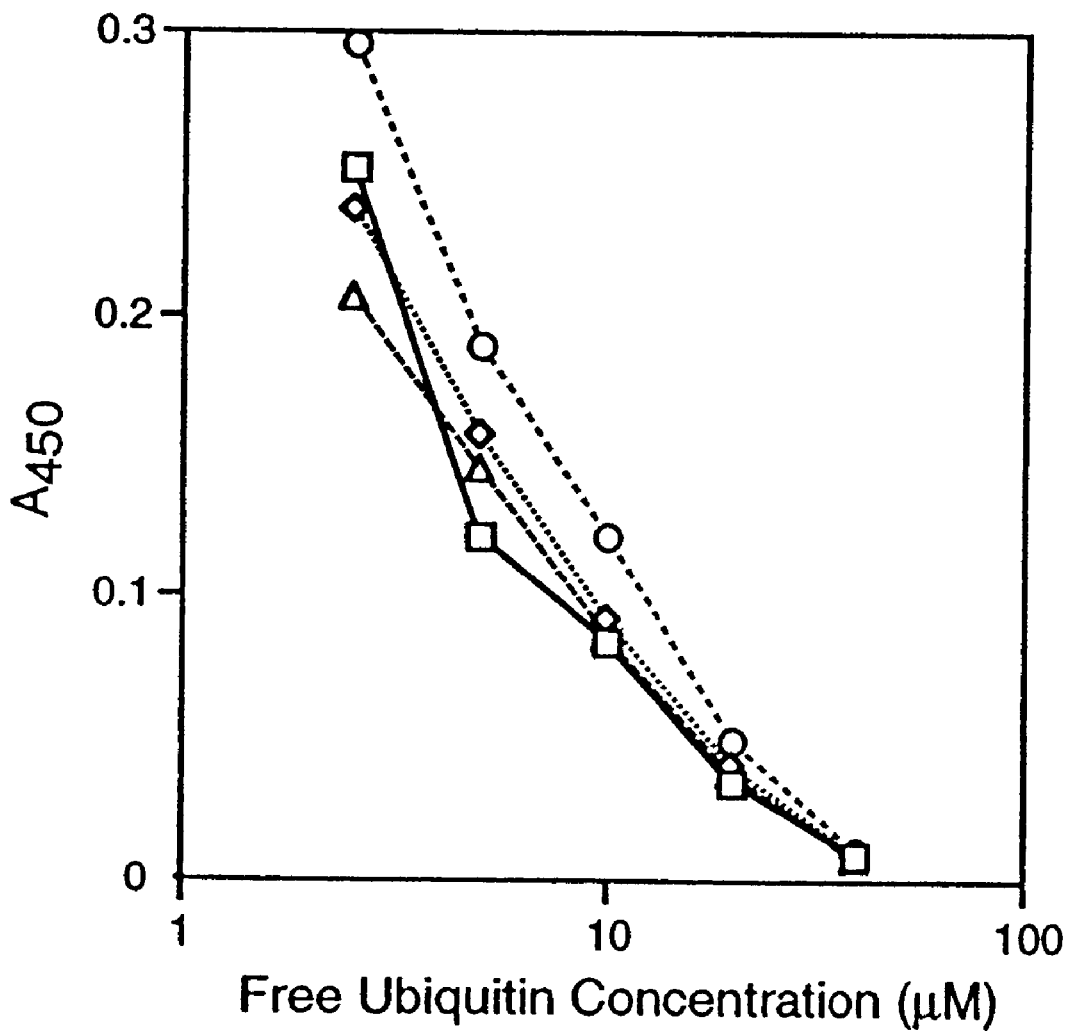
FIG. 11. Competition phage ELISA of ubiquitin-binding monobody 411. Experimental conditions are the same as described above for ubiquitin. The ELISA was performed in the presence of free ubiquitin in the binding solution. The experiments were performed with four different preparations of the same clone.

The 411 clone, which was the most enriched clone, was characterized using phage ELISA. The 411 clone showed selective binding and inhibition of binding in the presence of about 10 μM ubiquitin in solution (FIG. 11).

EXAMPLE XI

Methods for the Immobilization of Small Molecules

Target molecules were immobilized in wells of a microtiter plate (MAXISORP, Nunc) as described hereinbelow, and the wells were blocked with BSA. In addition to the use of carrier protein as described below, a conjugate of a target molecule in biotin can be made. The biotinylated ligand can then be immobilized to a microtiter plate well which has been coated with streptavidin.

In addition to the use of a carrier protein as described below, one could make a conjugate of a target molecule and biotin (Pierce) and immobilize a biotinylated ligand to a microtiter plate well which has been coated with streptavidin (Smith and Scott, 1993).

Small molecules may be conjugated with a carrier protein such as bovine serum albumin (BSA, Sigma), and passively adsorbed to the microtiter plate well. Alternatively, methods of chemical conjugation can also be used. In addition, solid supports other than microtiter plates can readily be employed.

EXAMPLE XII

Fluorescein Binding Monobody

Fluorescein has been used as a target for the selection of antibodies from combinatorial libraries (Barbas, et al. 1992). NHS-fluorescein was obtained from Pierce and used according to the manufacturer's instructions in preparing conjugates with BSA (Sigma). Two types of fluorescein-BSA conjugates were prepared with approximate molar ratios of 17 (fluorescein) to one (BSA).

The selection process was repeated 5–6 times to concentrate positive clones. In this experiment, the phage library was incubated with a protein mixture (BSA, cytochrome C (Sigma, Horse) and RNaseA (Sigma, Bovine), 1 mg/ml each) at room temperature for 30 minutes, prior to the addition to ligand coated wells. Bound phage were eluted in TBS containing 10 μM soluble fluorescein, instead of acid elution. After the final round, individual clones were picked and their binding affinities (see below) and DNA sequences were determined.

TABLE 4

| | BC | FG |
|---|---|---|
| | Clones from Library #2 | |
| WT | AVTVR (SEQ ID NO:47) | RGDSPAS (SEQ ID NO:48) |
| pLB24.1 | CNWRR (SEQ ID NO:49) | RAYRYRW (SEQ ID NO:50) |
| pLB24.2 | CMWRA (SEQ ID NO:51) | RWGMLRR (SEQ ID NO:52) |
| pLB24.3 | ARMRE (SEQ ID NO:53) | RWLRGRY (SEQ ID NO:54) |
| pLB24.4 | CARRR (SEQ ID NO:55) | RRAGWGW (SEQ ID NO:56) |
| pLB24.5 | CNWRR (SEQ ID NO:57) | RAYRYRW (SEQ ID NO:58) |
| pLB24.6 | RWRER (SEQ ID NO:59) | RHPWTER (SEQ ID NO:60) |
| pLB24.7 | CNWRR (SEQ ID NO:61) | RAYRYRW (SEQ ID NO:62) |
| pLB24.8 | ERRVP (SEQ ID NO:63) | RLLLWQR (SEQ ID NO:64) |
| pLB24.9 | GRGAG (SEQ ID NO:65) | FGSFERR (SEQ ID NO:66) |
| pLB24.11 | CRWTR (SEQ ID NO:67) | RRWFDGA (SEQ ID NO:68) |
| pLB24.12 | CNWRR (SEQ ID NO:69) | RAYRYRW (SEQ ID NO:70) |
| | Clones from Library #4 | |
| WT | AVTVR (SEQ ID NO:71) | GRGDS (SEQ ID NO:72) |
| pLB25.1 | GQRTF (SEQ ID NO:73) | RRWWA (SEQ ID NO:74) |
| pLB25.2 | GQRTF (SEQ ID NO:75) | RRWWA (SEQ ID NO:76) |
| pLB25.3 | GQRTF (SEQ ID NO:77) | RRWWA (SEQ ID NO:78) |
| pLB25.4 | LRYRS (SEQ ID NO:79) | GWRWR (SEQ ID NO:80) |
| pLB25.5 | GQRTF (SEQ ID NO:81) | RRWWA (SEQ ID NO:82) |
| pLB25.6 | GQRTF (SEQ ID NO:83) | RRWWA (SEQ ID NO:84) |
| pLB25.7 | LRYRS (SEQ ID NO:85) | GWRWR (SEQ ID NO:86) |
| pLB25.9 | LRYRS (SEQ ID NO:87) | GWRWR (SEQ ID NO:88) |
| pLB25.11 | GQRTF (SEQ ID NO:89) | RRWWA (SEQ ID NO:90) |
| pLB25.12 | LRYRS (SEQ ID NO:91) | GWRWR (SEQ ID NO:92) |

Figure 13:
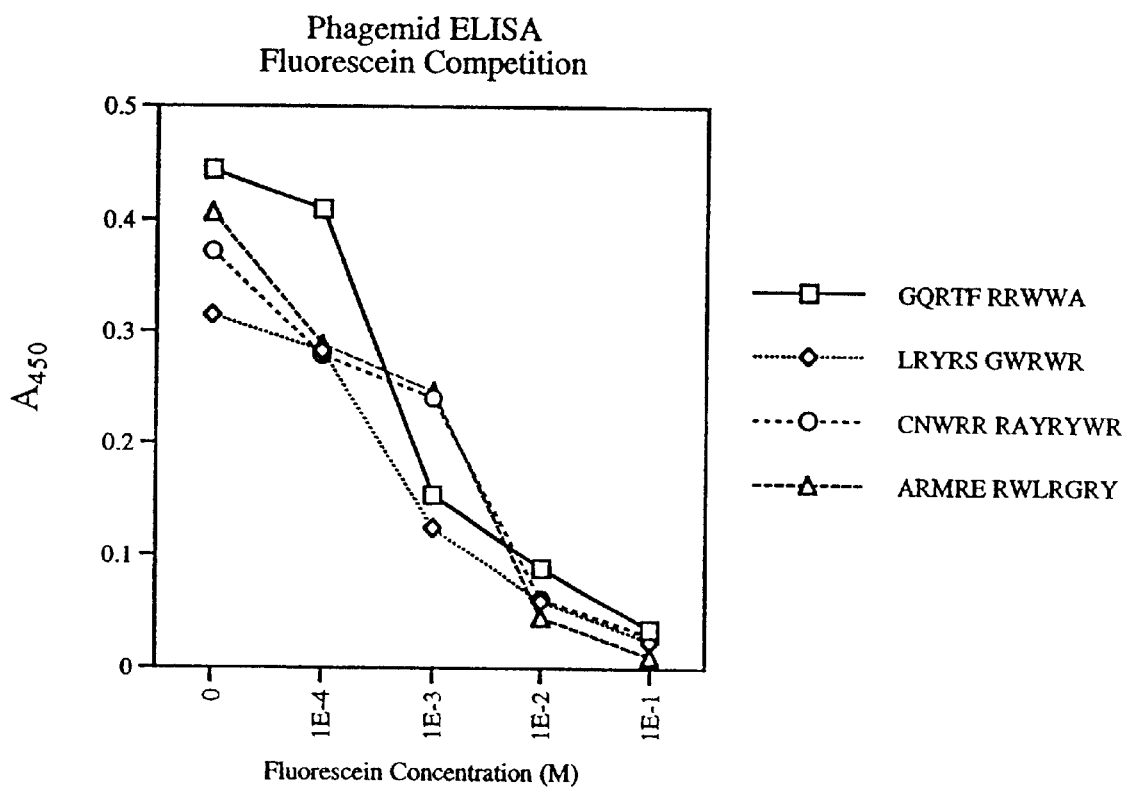
FIG. 13. (Fluorescein-2) Competition ELISA of the four clones. Experimental conditions are the same as ubiquitin-2 above.

Preliminary characterization of the binding affinities of selected clones were performed using phage ELISA and competition phage ELISA (see FIG. 12 (Fluorescein-1) and FIG. 13 (Fluorescein-2)). The four clones tested showed specific binding to the ligand-coated wells, and the binding reactions are inhibited by soluble fluorescein (see FIG. 13).

EXAMPLE XIII

Digoxigenin Binding Monobody

Digoxigenin-3-O-methyl-carbonyl-e-aminocapronic acid-NHS (Boehringer Mannheim) is used to prepare a digoxigenin-BSA conjugate. The coupling reaction is performed following the manufacturers' instructions. The digoxigenin-BSA conjugate is immobilized in the wells of a microtiter plate and used for panning. Panning is repeated 5 to 6 times to enrich binding clones. Because digoxigenin is sparingly soluble in aqueous solution, bound phages are eluted from the well using acidic solution. See Example XIV.

EXAMPLE XIV

TSAC (Transition State Analog Compound) Binding Monobodies

Carbonate hydrolyzing monobodies are selected as follows. A transition state analog for carbonate hydrolysis, 4-nitrophenyl phosphonate is synthesized by an Arbuzov reaction as described previously (Jacobs and Schultz, 1987). The phosphonate is then coupled to the carrier protein, BSA, using carbodiimide, followed by exhaustive dialysis (Jacobs and Schultz, 1987). The hapten-BSA conjugate is immobilized in the wells of a microtiter plate and monobody selection is performed as described above. Catalytic activities of selected monobodies are tested using 4-nitrophenyl carbonate as the substrate.

Other haptens useful to produce catalytic monobodies are summarized in H. Suzuki (1994) and in N. R. Thomas (1994).

EXAMPLE XV

NMR Characterization of Fn3 and Comparison of the Fn3 Secreted by Yeast with That Secreted by *E. coli*

Nuclear magnetic resonance (NMR) experiments are performed to identify the contact surface between FnAb and a target molecule, e.g., monobodies to fluorescein, ubiquitin, RNaseA and soluble derivatives of digoxigenin. The information is then be used to improve the affinity and specificity of the monobody. Purified monobody samples are dissolved in an appropriate buffer for NMR spectroscopy using Amicon ultrafiltration cell with a YM-3 membrane. Buffers are made with 90 % $H_2O$/10% $D_2O$ (distilled grade, Isotec) or with 100% $D_2O$. Deuterated compounds (e.g. acetate) are used to eliminate strong signals from them.

NMR experiments are performed on a Varian Unity INOVA 600 spectrometer equipped with four RF channels and a triple resonance probe with pulsed field gradient capability. NMR spectra are analyzed using processing programs such as FELIX (Molecular Simulations), NMRPIPE, PIPP, and CAPP (Garrett, et al., 1991; Delaglio, et al., 1995) on UNIX workstations. Sequence specific resonance assignments are made using well-established strategy using a set of triple resonance experiments (CBCA (CO)NH and HNCACB) (Grzesiek & Bax, 1992; Wittenkind & Mueller, 1993).

Nuclear Overhauser effect (NOE) is observed between $^1H$ nuclei closer than approximately 5 Å, which allows one to obtain information on interproton distances. A series of double- and triple-resonance experiments (Table 5; for recent reviews on these techniques, see Bax & Grzesiek, 1993 and Kay, 1995) are performed to collect distance (i.e. NOE) and dihedral angle (J-coupling) constraints. Isotope-filtered experiments are performed to determine resonance assignments of the bound ligand and to obtain distance constraints within the ligand and those between FnAb and the ligand. Details of sequence specific resonance assignments and NOE peak assignments have been described in detail elsewhere (Clore & Gronenborn, 1991; Pascal, et al., 1994b; Metzler, et al., 1996).

TABLE 5

NMR experiments for structure characterization

| Experiment Name | Reference |
|---|---|
| 1. reference spectra | |
| 2D-$^1H$, $^{15}N$-HSQC | (Bodenhausen & Ruben, 1980; Kay, et al., 1992) |
| 2D-$^1H$, $^{13}C$-HSQC | (Bodenhausen & Ruben, 1980; Vuister & Bax, 1992). |
| 2. backbone and side chain resonance assignments of $^{13}C/^{15}N$-labeled protein | |
| 3D-CBCA(CO)NH | (Grzesiek & Bax, 1992) |
| 3D-HNCACB | (Wittenkind & Mueller, 1993) |

TABLE 5-continued

NMR experiments for structure characterization

| Experiment Name | Reference |
|---|---|
| 3D-C(CO)NH | (Logan et al., 1992; Grzesiek et al., 1993) |
| 3D-H(CCO)NH | |
| 3D-HBHA(CBCACO)NH | (Grzesiek & Bax, 1993) |
| 3D-HCCH-TOCSY | (Kay et al., 1993) |
| 3D-HCCH-COSY | (Ikura et al., 1991) |
| 3D-$^1$H, $^{15}$N-TOCSY-HSQC | (Zhang et al., 1994) |
| 2D-HB(CBCDCE)HE | (Yamazaki et al., 1993) |

3. resonance assignments of unlabeled ligand

| | |
|---|---|
| 2D-isotope-filtered $^1$H-TOCSY | |
| 2D-isotope-filtered $^1$H-COSY | |
| 2D-isotope-filtered $^1$H-NOESY | (Ikura & Bax, 1992) |

4. structural constraints within labeled protein

| | |
|---|---|
| 3D-$^1$H, $^{15}$N-NOESY-HSQC | (Zhang et al., 1994) |
| 4D-$^1$H, $^{13}$C-HMQC-NOESY-HMQC | (Vuister et al., 1993) |
| 4D-$^1$H, $^{13}$C, $^{15}$N-HSQC-NOESY-HSQC | (Muhandiram el al., 1993; Pascal et al., 1994a) | within unlabeled ligand

| | |
|---|---|
| 2D-isotope-filtered $^1$H-NOESY | (Ikura & Bax, 1992) | interactions between protein and ligand

| | |
|---|---|
| 3D-isotope-filtered $^1$H, $^{15}$N-NOESY-HSQC | |
| 3D-isotope-filtered $^1$H, $^{13}$C-NOESY-HSQC | (Lee et al., 1994) |

5. dihedral angle constraints

| | |
|---|---|
| J-molulated $^1$H, $^{15}$N-HSQC | (Billeter et al., 1992) |
| 3D-HNHB | (Archer et al., 1991) |

Backbone $^1$H, $^{15}$N and $^{13}$C resonance assignments for a monobody are compared to those for wild-type Fn3 to assess structural changes in the mutant. Once these data establish that the mutant retains the global structure, structural refinement is performed using experimental NOE data Because the structural difference of a monobody is expected to be minor, the wild-type structure can be used as the initial model after modifying the amino acid sequence. The mutations are introduced to the wild-type structure by interactive molecular modeling, and then the structure is energy-minimized using a molecular modeling program such as QUANTA (Molecular Simulations). Solution structure is refined using cycles of dynamical simulated annealing (Nilges et al., 1988) in the program X-PLOR (Brünger, 1992). Typically, an ensemble of fifty structures is calculated. The validity of the refined structures is confirmed by calculating a fewer number of structures from randomly generated initial structures in X-PLOR using the YASAP protocol (Nilges, et al, 1991). Structure of a monobody-ligand complex is calculated by first refining both components individually using intramolecular NOEs, and then docking the two using intermolecular NOEs.

Figure 14:
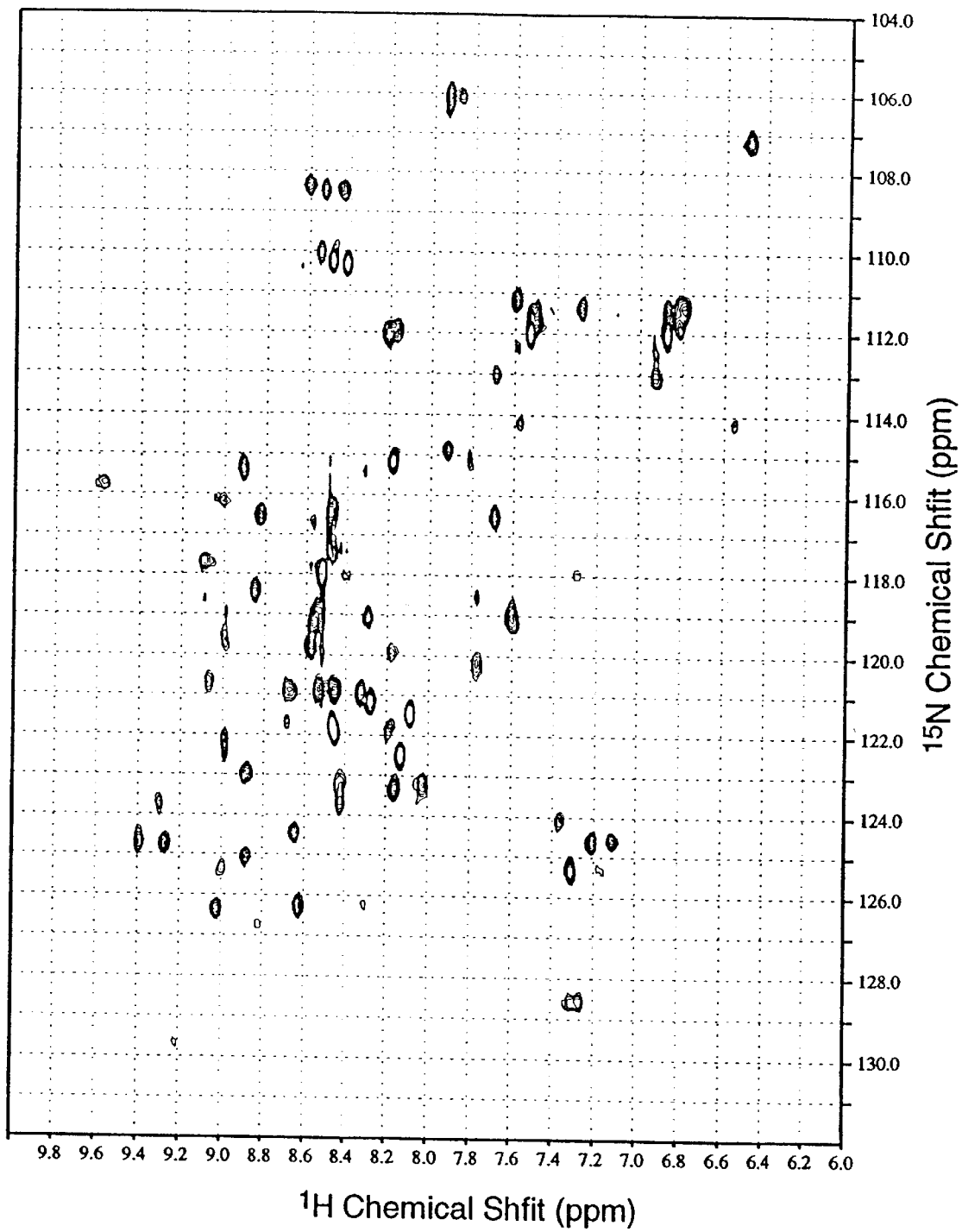
FIG. 14. $^1H$, $^{15}N$-HSQC spectrum of a fluorescence-binding monobody LB25.5. Approximately 20 μm protein was dissolved in 10 mm sodium acetate buffer (pH 5.0) containing 100 mM sodium chloride. The spectrum was collected at 30° C. on a Varian Unity INOVA 600 NMR spectrometer.

For example, the $^1$H, $^{15}$N-HSQC spectrum for the fluorescein-binding monobody LB25.5 is shown in FIG. 14. The spectrum shows a good dispersion (peaks are spread out) indicating that LB25.5 is folded into a globular conformation.

Further, the spectrum resembles that for the wild-type Fn3, showing that the overall structure of LB25.5 is similar to that of Fn3. These results demonstrate that ligand-binding monobodies can be obtained without changing the global fold of the Fn3 scaffold.

Chemical shift perturbation experiments are performed by forming the complex between an isotope-labeled FnAb and an unlabeled ligand. The formation of a stoichiometric complex is followed by recording the HSQC spectrum. Because chemical shift is extremely sensitive to nuclear environment, formation of a complex usually results in substantial chemical shift changes for resonances of amino acid residues in the interface. Isotope-edited NMR experiments (2D HSQC and 3D CBCA(CO)NH) are used to identify the resonances that are perturbed in the labeled component of the complex; i.e. the monobody. Although the possibility of artifacts due to long-range conformational changes must always be considered, substantial differences for residues clustered on continuous surfaces are most likely to arise from direct contacts (Chen et al., 1993; Gronenborn & Clore, 1993).

An alternative method for mapping the interaction surface utilizes amide hydrogen exchange (HX) measurements. HX rates for each amide proton are measured for $^{15}$N labeled monobody both free and complexed with a ligand. Ligand binding is expected to result in decreased amide HX rates for monobody residues in the interface between the two proteins, thus identifying the binding surface. HX rates for monobodies in the complex are measured by allowing HX to occur for a variable time following transfer of the complex to $D_2O$; the complex is dissociated by lowering pH and the HSQC spectrum is recorded at low pH where amide HX is slow. Fn3 is stable and soluble at low pH, satisfying the prerequisite for the experiments.

EXAMPLE XVI

Construction and Analysis of Fn3-Display System Specific for Ubiquitin

An Fn3-display system was designed and synthesized, ubiquitin-binding clones were isolated and a major Fn3 mutant in these clones was biophysically characterized.

Gene construction and phage display of Fn3 was performed as in Examples I and II above. The Fn3-phage pIII fusion protein was expressed from a phagemid-display vector, while the other components of the M13 phage, including the wildtype pIII, were produced using a helper phage (Bass et al., 1990). Thus, a phage produced by this system should contain less than one copy of Fn3 displayed on the surface. The surface display of Fn3 on the phage was detected by ELISA using an anti-Fn3 antibody. Only phages containing the Fn3-pIII fusion vector reacted with the antibody.

After confirming the phage surface to display Fn3, a phage display library of Fn3 was constructed as in Example III. Random sequences were introduced in the BC and FG loops. In the first library, five residues (77–81) were randomized and three residues (82–84) were deleted from the FG loop. The deletion was intended to reduce the flexibility and improve the binding affinity of the FG loop. Five residues (26–30) were also randomized in the BC loop in order to provide a larger contact surface with the target molecule. Thus, the resulting library contains five randomized residues in each of the BC and FG loops (Table 6). This library contained approximately $10^8$ independent clones.

Library Screening

Library screening was performed using ubiquitin as the target molecule. In each round of panning, Fn3-phages were absorbed to a ubiquitin-coated surface, and bound phages were eluted competitively with soluble ubiquitin. The recovery ratio improved from $4.3 \times 10^{-7}$ in the second round to $4.5 \times 10^{-6}$ in the fifth round, suggesting an enrichment of binding clones. After five founds of panning, the amino acid sequences of individual clones were determined (Table 6).

TABLE 6

Sequences in the variegated loops of enriched clones

| Name | BC loop | FG loop | Frequency |
|---|---|---|---|
| Wild Type | GCAGTTACCGTGCGT (SEQ ID NO:93) AlaValThrValArg (SEQ ID NO:94) | GGCCGTGGTGACAGCCCAGCGAGC (SEQ ID NO:95) GlyArgGlyAspSerProAlaSer (SEQ ID NO:96) | — |
| Library[a] | NNKNNKNNKNNKNNK X X X X X | NNKNNKNNKNNKNNK--------- X X X X X (deletion) | — |
| clone1 (Ubi4) | TCGAGGTTGCGGCGG (SEQ ID NO:97) SerArgLeuArgArg (SEQ ID NO:98) | CCGCCGTGGAGGGTG (SEQ ID NO:99) ProProTrpArgVal (SEQ ID NO:100) | 9 |
| clone2 | GGTCAGCGAACTTTT (SEQ ID NO:101) GlyGlnArgThrPhe (SEQ ID NO:102) | AGGCGGTGGTGGGCT (SEQ ID NO:103) ArgArgTrpTrpAla (SEQ ID NO:104) | 1 |
| clone3 | GCGAGGTGGACGCTT (SEQ ID NO:105) AlaArgTrpThrLeu (SEQ ID NO:106) | AGGCGGTGGTGGTGG (SEQ ID NO:107) ArgArgTrpTrpTrp (SEQ ID NO:108) | 1 |

N denotes an equimolar mixture of A, T, G and C; K denotes an equimolar mixture of G and T.

A clone, dubbed Ubi4, dominated the enriched pool of Fn3 variants. Therefore, further investigation was focused on this Ubi4 clone. Ubi4 contains four mutations in the BC loop (Arg 30 in the BC loop was conserved) and five mutations and three deletions in the FG loop. Thus 13% (12 out of 94) of the residues were altered in Ubi4 from the wild-type sequence.

FIG. 15 shows a phage ELISA analysis of Ubi4. The Ubi4 phage binds to the target molecule, ubiquitin, with a significant affinity, while a phage displaying the wild-type Fn3 domain or a phase with no displayed molecules show little detectable binding to ubiquitin (FIG. 15a). In addition, the Ubi4 phage showed a somewhat elevated level of background binding to the control surface lacking the ubiquitin coating. A competition ELISA experiments shows the $IC_{50}$ (concentration of the free ligand which causes 50% inhibition of binding) of the binding reaction is approximately 5 $\mu$M (FIG. 15b). BSA, bovine ribonuclease A and cytochrome C show little inhibition of the Ubi4-ubiquitin binding reaction (FIG. 15c), indicating that the binding reaction of Ubi4 to ubiquitin does result from specific binding.

Characterization of a Mutant Fn3 Protein

The expression system yielded 50–100 mg Fn3 protein per liter culture. A similar level of protein expression was observed for the Ubi4 clone and other mutant Fn3 proteins.

Ubi4-Fn3 was expressed as an independent protein. Though a majority of Ubi4 was expressed in E. coli as a soluble protein, its solubility was found to be significantly reduced as compared to that of wild-type Fn3. Ubi4 was soluble up to ~20 $\mu$M at low pH, with much lower solubility at neutral pH. This solubility was not high enough for detailed structural characterization using NMR spectroscopy or X-ray crystallography.

The solubility of the Ubi4 protein was improved by adding a solubility tail, GKKGK, as a C-terminal extension. The gene for Ubi4-Fn3 was subcloned into the expression vector pAS45 using PCR. The C-terminal solubilization tag, GKKGK, was incorporated in this step. E. coli BL21 (DE3) (Novagen) was transformed with the expression vector (pAS45 and its derivatives). Cells were grown in M9 minimal media and M9 media supplemented with Bactotryptone (Difco) containing ampicillin (200 $\mu$g/ml). For isotopic labeling, $^{15}$N NH$_4$Cl replaced unlabeled NH$_4$Cl in the media 500 ml medium in a 2 liter baffle flask was inoculated with 10 ml of overnight culture and agitated at 37° C. IPTG was added at a final concentration of 1 mM to initiate protein expression when OD (600 nm) reaches one. The cells were harvested by centrifugation 3 hours after the addition of IPTG and kept frozen at 70° C. until used.

Proteins were purified as follows. Cells were suspended in 5 ml/(g cell) of Tris (50 mM, pH 7.6) containing phenylmethylsulfonyl fluoride (1 mM). Hen egg lysozyme (Sigma) was added to a final concentration of 0.5 mg/ml. After incubating the solution for 30 minutes at 37° C., it was sonicated three times for 30 seconds on ice. Cell debris was removed by centrifugation. Concentrated sodium chloride was added to the solution to a final concentration of 0.5 M. The solution was applied to a HI-TRAP chelating column (Pharmacia) preloaded with nickel and equilibrated in the Tris buffer containing sodium chloride (0.5 M). After washing the column with the buffer, histag-Fn3 was eluted with the buffer containing 500 mM imidazole. The protein was further purified using a RESOURCES® column (Pharmacia) with a NaCl gradient in a sodium acetate buffer (20 mM, pH 4.6).

With the GKKGK (SEQ ID NO:109) tail, the solubility of the Ubi4 protein was increased to over 1 mM at low pH and up to ~50 $\mu$M at neutral pH. Therefore, further analyses were performed on Ubi4 with this C-terminal extension (hereafter referred to as Ubi4-K). It has been reported that the solubility of a minibody could be significantly improved by addition of three Lys residues at the N- or C-termini (Bianchi et al., 1994). In the case of protein Rop, a non-structured C-terminal tail is critical in maintaining its solubility (Smith et al., 1995).

Oligomerization states of the Ubi4 protein were determined using a size exclusion column. The wild-type Fn3 protein was monomeric at low and neutral pH's. However, the peak of the Ubi4-K protein was significantly broader than that of wild-type Fn3, and eluted after the wild-type protein. This suggests interactions between Ubi4-K and the column material, precluding the use of size exclusion chromatography to determine the oligomerization state of Ubi4. NMR studies suggest that the protein is monomeric at low pH.

Figure 15B:
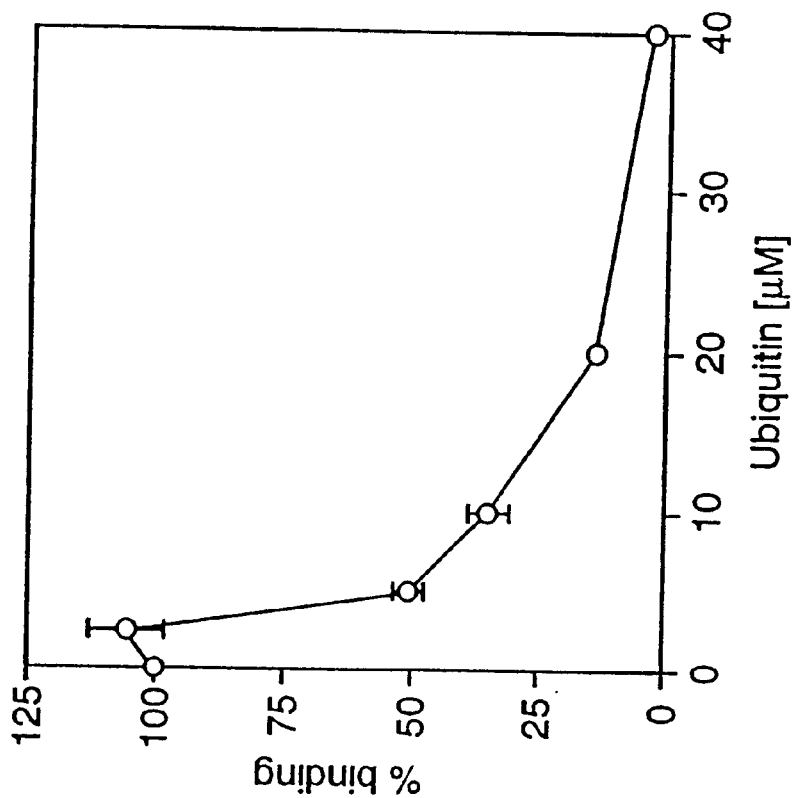
FIG. 15B. Competition phage ELISA of Ubi4-Fn3. Ubi4-Fn3 phages were preincubated with soluble ubiquitin at an indicated concentration, followed by the phage ELISA detection in ubiquitin-coated wells.
Figure 15A:
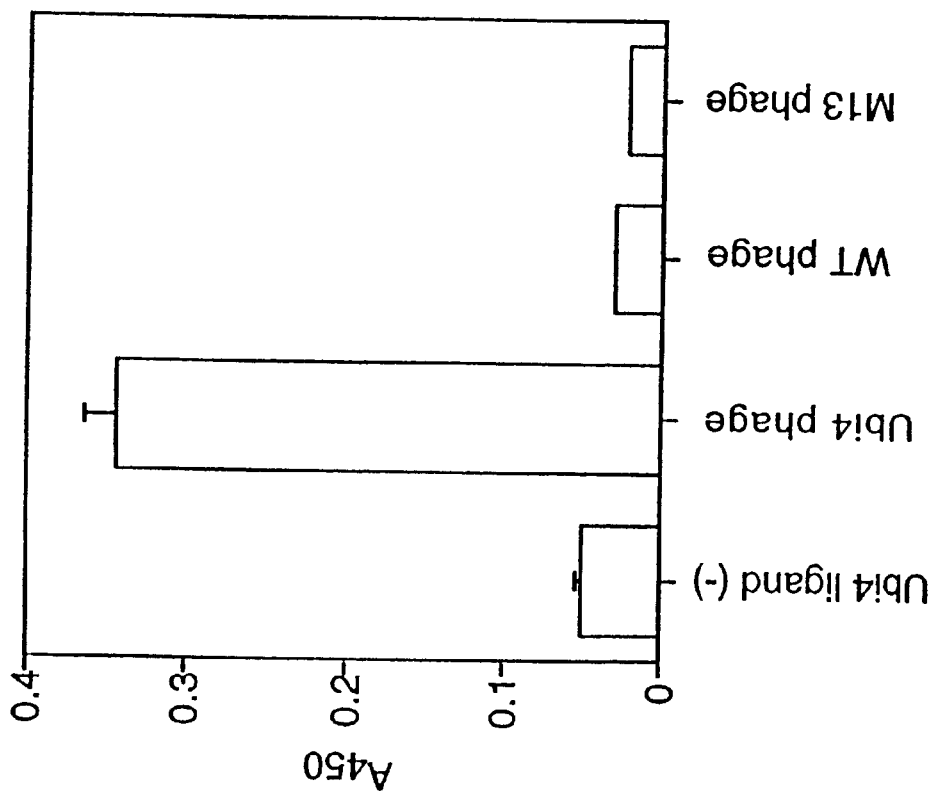
FIG. 15A. Characterization of the binding reaction of Ubi4-Fn3 to the target, ubiquitin. Phage ELISA analysis of binding of Ubi4-Fn3 to ubiquitin. The binding of Ubi4-phages to ubiquitin-coated wells was measured. The control experiment was performed with wells containing no ubiquitin.
Figure 15D:
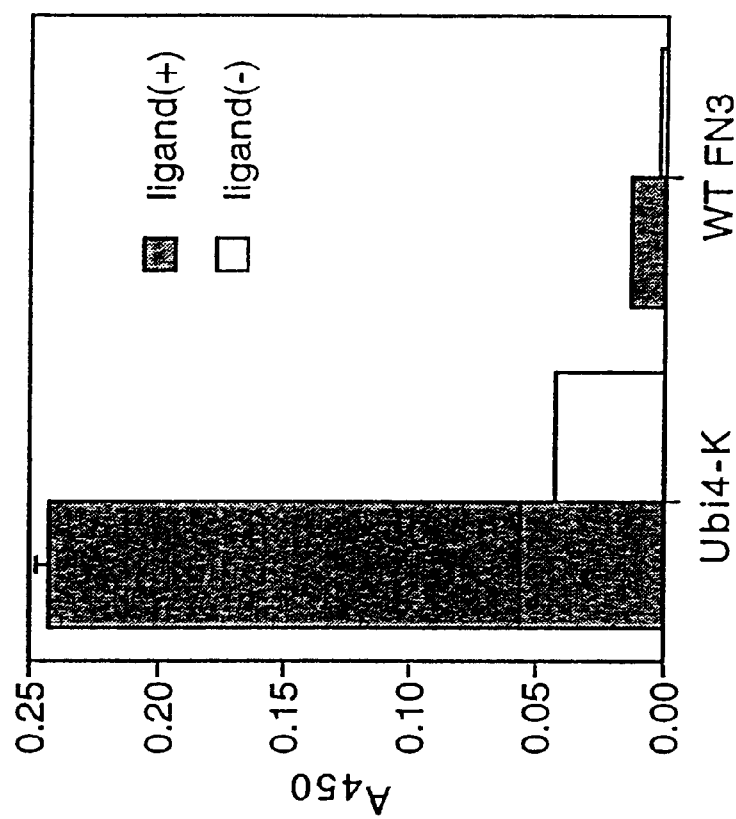
FIG. 15D. ELISA using free proteins.
Figure 15C:
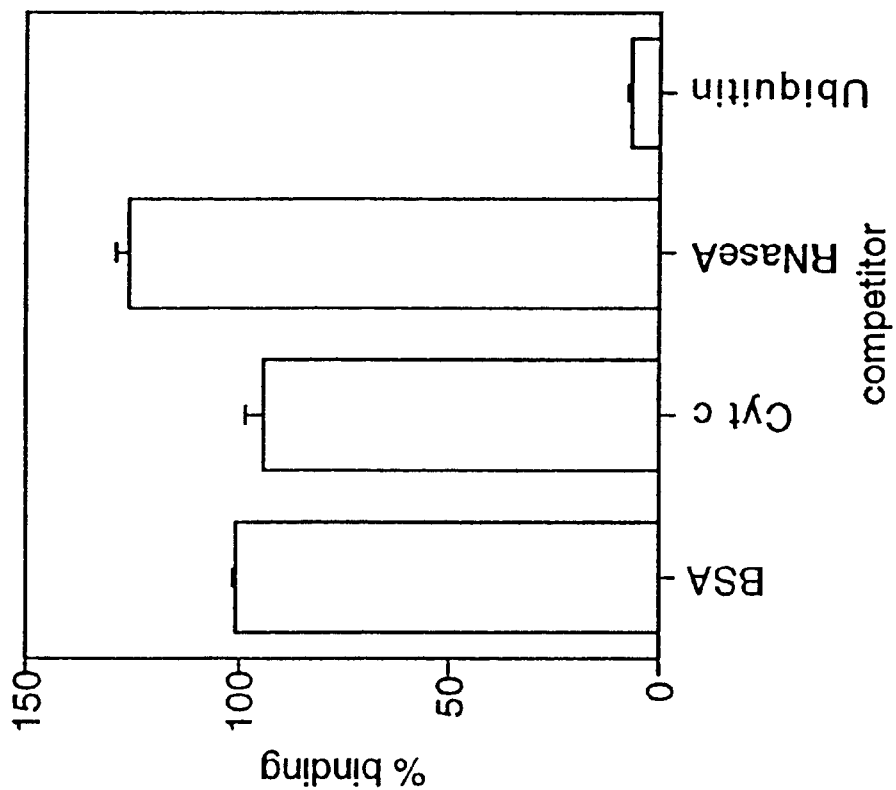
FIG. 15C. Competition phage ELISA testing the specificity of the Ubi4 clone. The Ubi4 phages were preincubated with 250 µg/ml of soluble proteins, followed by phage ELISA as in (b).

The Ubi4-K protein retained a binding affinity to ubiquitin as judged by ELISA (FIG. 15d). However, an attempt to determine the dissociation constant using a biosensor (Affinity Sensors, Cambridge, U.K.) failed because of high background binding of Ubi4-K-Fn3 to the sensor matrix. This matrix mainly consists of dextran, consistent with our observation that interactions between Ubi4-K interacts with the cross-linked dextran of the size exclusion column.

EXAMPLE XVII

Stability Measurements of Monobodies

Guanidine hydrochloride (GuHCl)-induced unfolding and refolding reactions were followed by measuring tryptophan fluorescence. Experiments were performed on a Spectronic AB-2 spectrofluorometer equipped with a motor-driven syringe (Hamilton Co.). The cuvette temperature was kept at 30° C. The spectrofluorometer and the syringe were controlled by a single computer using a home-built interface. This system automatically records a series of spectra following GuHCl titration. An experiment started with a 1.5 ml buffer solution containing 5 $\mu$M protein. An emission spectrum (300–400 nm; excitation at 290 nm) was recorded following a delay (3–5 minutes) after each injection (50 or 100 $\mu$l) of a buffer solution containing GuHCl. These steps were repeated until the solution volume reached the full capacity of a cuvette (3.0 ml). Fluorescence intensities were normalized as ratios to the intensity at an isofluorescent point which was determined in separate experiments. Unfolding curves were fitted with a two-state model using a nonlinear least-squares routine (Santoro & Bolen, 1988). No significant differences were observed between experiments with delay times (between an injection and the start of spectrum acquisition) of 2 minutes and 10 minutes, indicating that the unfolding/refolding reactions reached close to an equilibrium at each concentration point within the delay times used.

Figure 16:
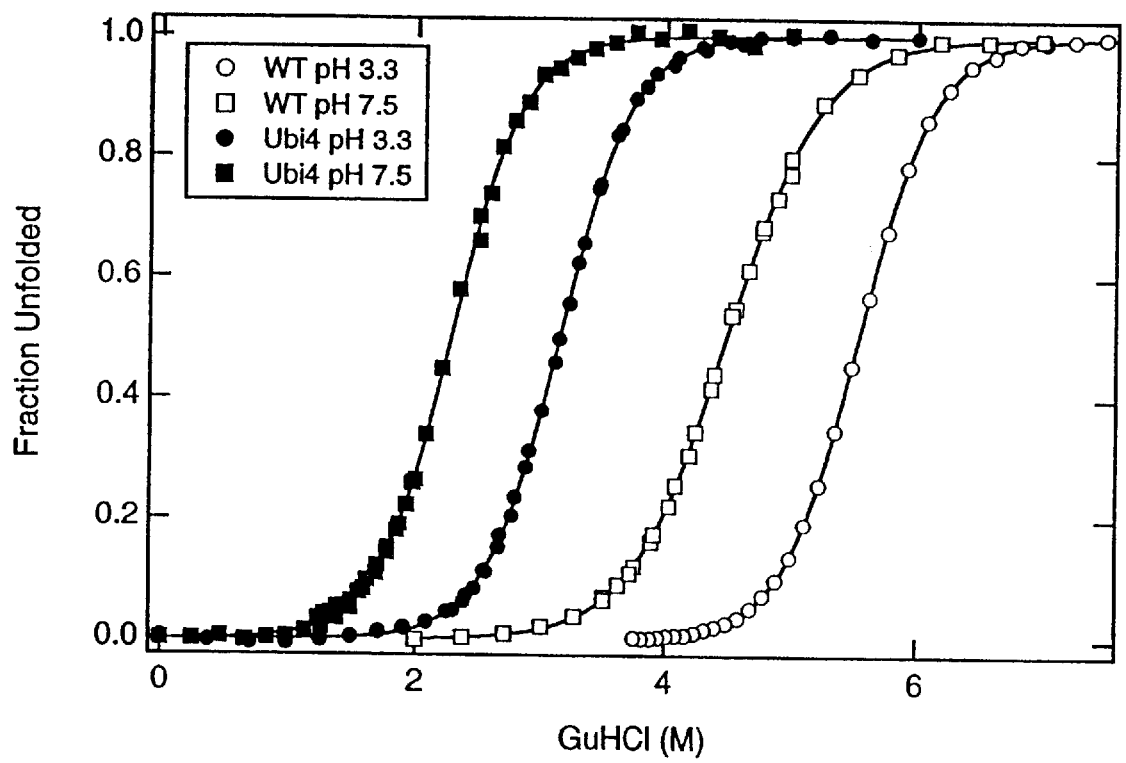
FIG. 16. Equilibrium unfolding curves for Ubi4-Fn3 (closed symbols) and wild-type Fn3 (open symbols). Squares indicate data measured in TBS (Tris HCl buffer (50 mM, pH 7.5) containing NaCl (150 mM)). Circles indicate data measured in Gly HCl buffer (20 mM, pH 3.3) containing NaCl (300 mM). The curves show the best fit of the transition curve based on the two-state model. Parameters characterizing the transitions are listed in Table 7.

Conformational stability of Ubi4-K was measured using above-described GuHCl-induced unfolding method. The measurements were performed under two sets of conditions; first at pH 3.3 in the presence of 300 mM sodium chloride, where Ubi4-K is highly soluble, and second in TBS, which was used for library screening. Under both conditions, the unfolding reaction was reversible, and we detected no signs of aggregation or irreversible unfolding. FIG. 16 shows unfolding transitions of Ubi4-K and wild-type Fn3 with the N-terminal (his)$_6$ tag and the C-terminal solubility tag. The stability of wild-type Fn3 was not significantly affected by the addition of these tags. Parameters characterizing the unfolding transitions are listed in Table 7.

TABLE 7

Stability parameters for Ubi4 and wild-type Fn3 as determined by GuHCl-induced unfolding

| Protein | $\Delta G_0$ (kcal mol$^{-1}$) | $m_G$ (kcal mol$^{-1}$ M$^{-1}$) |
| --- | --- | --- |
| Ubi4 (pH 7.5) | 4.8 ± 0.1 | 2.12 ± 0.04 |
| Ubi4 (pH 3.3) | 6.5 ± 0.1 | 2.07 ± 0.02 |
| Wild-type (pH 7.5) | 7.2 ± 0.2 | 1.60 ± 0.04 |
| Wild-type (pH 3.3) | 11.2 ± 0.1 | 2.03 ± 0.02 |

$\Delta G_0$ is the free energy of unfolding in the absence of denaturant;
$m_G$ is the dependence of the free energy of unfolding on GuHCl concentration.
For solution conditions, see FIG. 4 caption.

Though the introduced mutations in the two loops certainly decreased the stability of Ubi4-K relative to wild-type Fn3, the stability of Ubi4 remains comparable to that of a "typical" globular protein. It should also be noted that the stabilities of the wild-type and Ubi4-K proteins were higher at pH 3.3 than at pH 7.5.

The Ubi4 protein had a significantly reduced solubility as compared to that of wild-type Fn3, but the solubility was improved by the addition of a solubility tail. Since the two mutated loops comprise the only differences between the wild-type and Ubi4 proteins, these loops must be the origin of the reduced solubility. At this point, it is not clear whether the aggregation of Ubi4-K is caused by interactions between the loops, or by interactions between the loops and the invariable regions of the Fn3 scaffold.

The Ubi4-K protein retained the global fold of Fn3, showing that this scaffold can accommodate a large number of mutations in the two loops tested. Though the stability of the Ubi4-K protein is significantly lower than that of the wild-type Fn3 protein, the Ubi4 protein still has a conformational stability comparable to those for small globular proteins. The use of a highly stable domain as a scaffold is clearly advantageous for introducing mutations without affecting the global fold of the scaffold. In addition, the GuHCl-induced unfolding of the Ubi4 protein is almost completely reversible. This allows the preparation of a correctly folded protein even when a Fn3 mutant is expressed in a misfolded form, as in inclusion bodies. The modest stability of Ubi4 in the conditions used for library screening indicates that Fn3 variants are folded on the phage surface. This suggests that a Fn3 clone is selected by its binding affinity in the folded form, not in a denatured form. Dickinson et al. proposed that Val 29 and Arg 30 in the BC loop stabilize Fn3. Val 29 makes contact with the hydrophobic core, and Arg 30 forms hydrogen bonds with Gly 52 and Val 75. In Ubi4-Fn3, Val 29 is replaced with Arg, while Arg 30 is conserved. The FG loop was also mutated in the library. This loop is flexible in the wild-type structure, and shows a large variation in length among human Fn3 domains (Main et al., 1992). These observations suggest that mutations in the FG loop may have less impact on stability. In addition, the N-terminal tail of Fn3 is adjacent to the molecular surface formed by the BC and FG loops (FIGS. 1 and 17) and does not form a well-defined structure. Mutations in the N-terminal tail would not be expected to have strong detrimental effects on stability. Thus, residues in the N-terminal tail may be good sites for introducing additional mutations.

EXAMPLE XVIII

NMR Spectroscopy of Ubi4-Fn3

Ubi4-Fn3 was dissolved in [$^2$H]-Gly HCl buffer (20 mM, pH 3.3) containing NaCl (300 mM) using an Amicon ultrafiltration unit. The final protein concentration was 1 mM. NMR experiments were performed on a Varian Unity INOVA 600 spectrometer equipped with a triple-resonance probe with pulsed field gradient. The probe temperature was set at 30° C. HSQC, TOCSY-HSQC and NOESY-HSQC spectra were recorded using published procedures (Kay et al., 1992; Zhang et al., 1994). NMR spectra were processed and analyzed using the NMRPIPE and NMRVIEW software (Johnson & Blevins, 1994; Delaglio et al., 1995) on UNIX workstations. Sequence-specific resonance assignments were made using standard procedures (Wüithrich, 1986; Clore & Gronenbom, 1991). The assignments for wild-type Fn3 (Baron et al., 1992) were confirmed using a $^{15}$N-labeled protein dissolved in sodium acetate buffer (50 mM, pH 4.6) at 30° C.

Figure 17A:
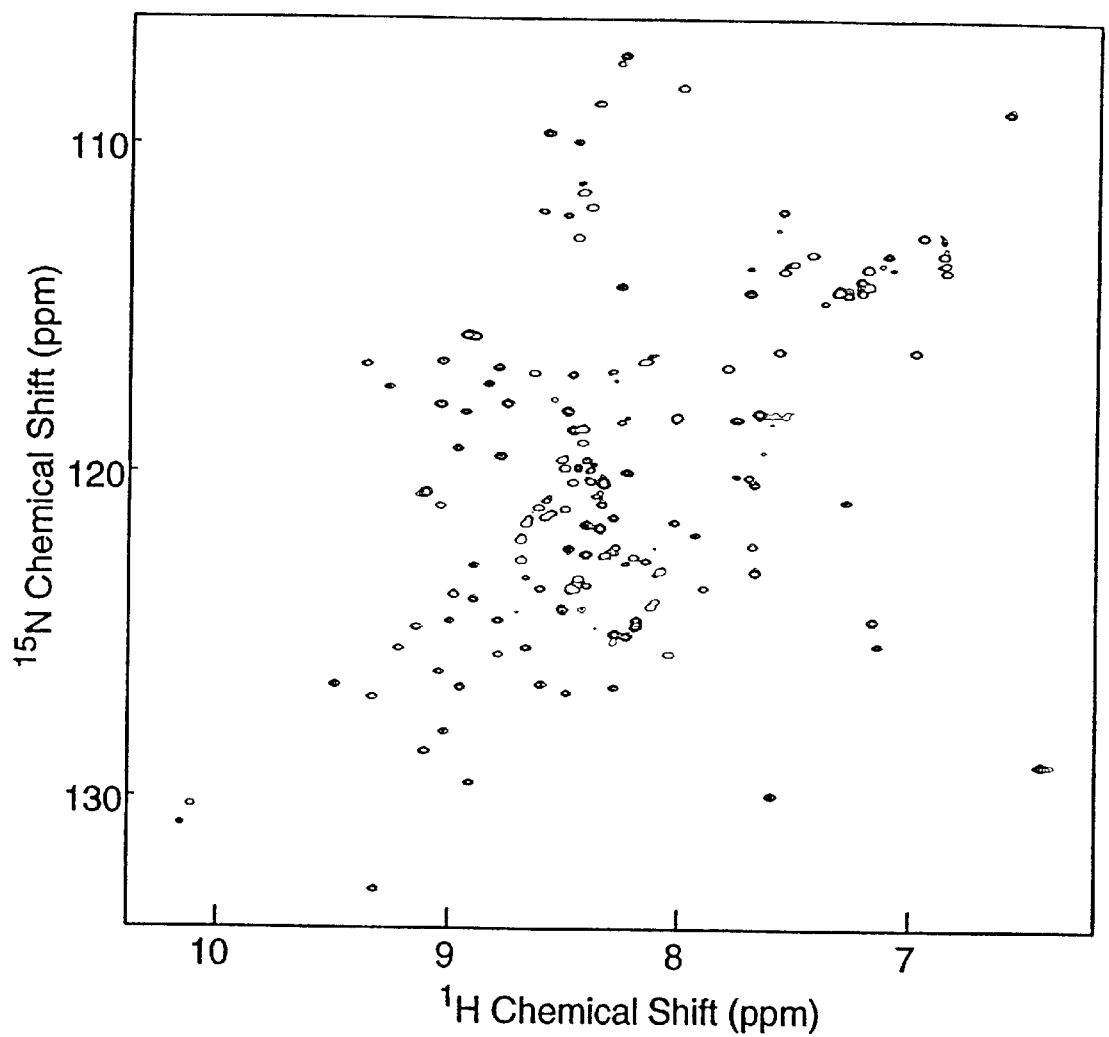
FIG. 17. (a) $^1$H, $^{15}$N-HSQC spectrum of [$^{15}$N]-Ubi4-K Fn3. (b). Difference ($\delta_{wild-type} - \Delta_{Ubi4}$) of $^1$H (b) and $^{15}$N (c) chemical shifts plotted versus residue number. Values for residues 82–84 (shown as filled circles) where Ubi4-K deletions are set to zero. Open circles indicate residues that are mutated in the Ubi4-K protein. The locations of β-strands are indicated with arrows.
Figure 17B:
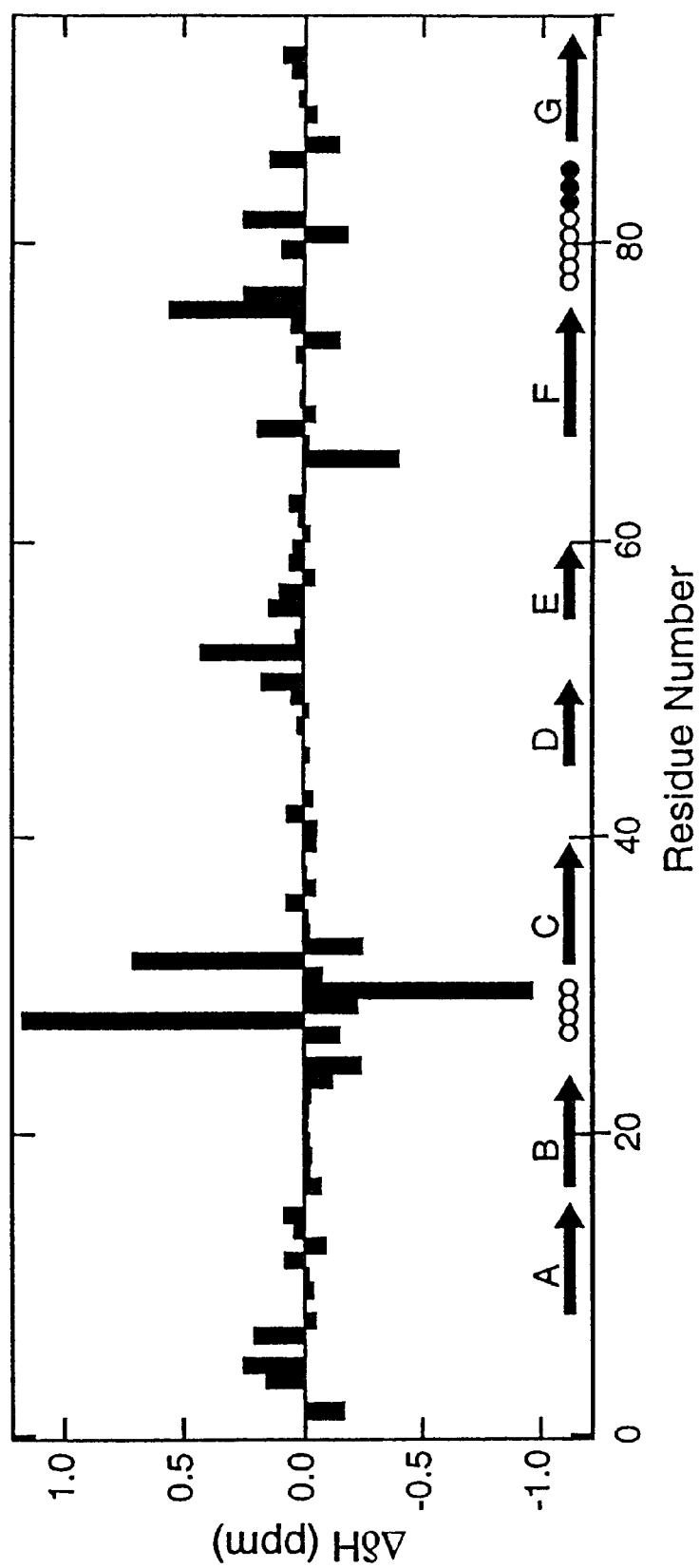
Figure 17C:
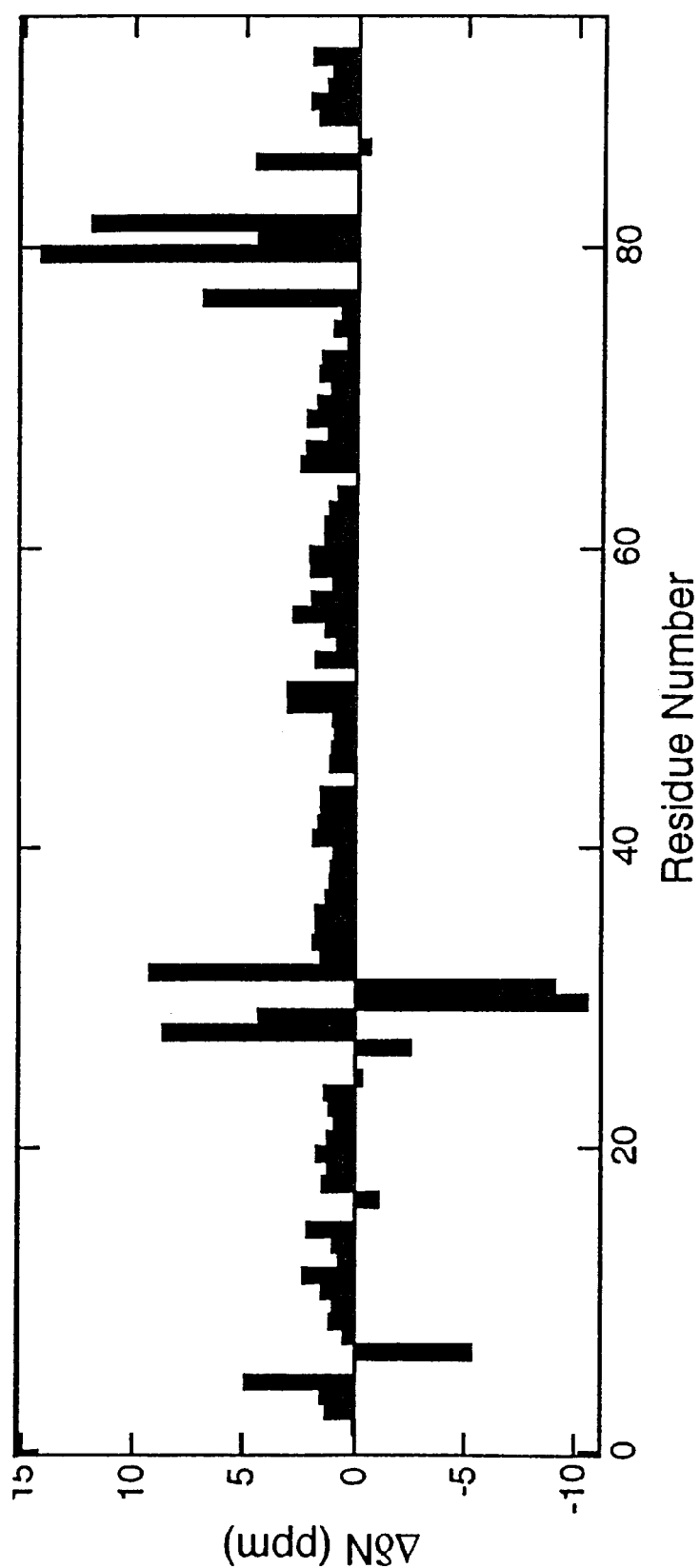

The three-dimensional structure of Ubi4-K was characterized using this heteronuclear NMR spectroscopy method. A high quality spectrum could be collected on a 1 mM solution of $^{15}$N-labeled Ubi4 (FIG. 17a) at low pH. The linewidth of amide peaks of Ubi4-K was similar to that of wild-type Fn3, suggesting that Ubi4-K is monomeric under the conditions used. Complete assignments for backbone $^1$H and $^{15}$N nuclei were achieved using standard $^1$H, $^{15}$N double resonance techniques, except for a row of His residues in the N-terminal (His)$_6$ tag. There were a few weak peaks in the HSQC spectrum which appeared to originate from a minor species containing the N-terminal Met residue. Mass spectroscopy analysis showed that a majority of Ubi4-K does not contain the N-terminal Met residue. FIG. 17 shows differences in $^1$HN and $^{15}$N chemical shifts between Ubi4-K and wild-type Fn3. Only small differences are observed in the chemical shifts, except for those in and near the mutated BC and FG loops. These results clearly indicate that Ubi4-K retains the global fold of Fn3, despite the extensive mutations in the two loops. A few residues in the N-terminal region, which is close to the two mutated loops, also exhibit significant chemical differences between the two proteins. An HSQC spectrum was also recorded on a 50 μM sample of Ubi4-K in TBS. The spectrum was similar to that collected at low pH, indicating that the global conformation of Ubi4 is maintained between pH 7.5 and 3.3.

The complete disclosure of all patents, patent documents and publications cited herein are incorporated by reference as if individually incorporated. The foregoing detailed description and examples have been given for clarity of understanding only. No unnecessary limitations are to be understood therefrom. The invention is not limited to the exact details shown and described for variations obvious to one skilled in the art will be included within the invention defined by the claims.

What is claimed is:

1. A fibronectin-peptide display library comprising fibronectin type III (Fn3) polypeptide monobodies, each Fn3 polypeptide monobody comprising at least two Fn3 β-strand domain sequences with a loop region sequence linked between each Fn3 β-strand domain sequence, wherein at least one monobody loop region sequence varies as compared to the wild-tyne (SEQ ID NO:110, FIG. 2) loop region sequence by deletion of two to twelve amino acids in the loop region sequence, insertion of at least two to 25 amino acids, or replacement of at least two amino acids in the loop region sequence, and wherein the polypeptide monobody loop region comprises a peptide with at least two amino acids that binds to a specific binding partner (SBP) to form a polypeptide:SBP complex.

2. The fibronectin-peptide display library of claim 1, wherein the peptide is displayed on the surface of a bacteriophage or virus.

3. The fibronectin-peptide display library of claim 2, wherein the bacteriophage is M13 or fd.

* * * * *

UNITED STATES PATENT AND TRADEMARK OFFICE
CERTIFICATE OF CORRECTION

PATENT NO. : 6,703,199 B1
DATED : March 9, 2004
INVENTOR(S) : Shohei Koide

It is certified that error appears in the above-identified patent and that said Letters Patent is hereby corrected as shown below:

Title page,
Item [56], References Cited, OTHER PUBLICATIONS, "Burgess et al." reference, please delete "Mutagensis" and insert -- Mutagenesis -- therefor;
"Lazar et al." reference, please delete "Activites" and insert -- Activities -- therefor;
"Winter" reference, please delete "Displa" and insert -- Display -- therefor;

Column 107,
Line 39, please delete "tyne" and insert -- type -- therefor.

Signed and Sealed this

Eleventh Day of January, 2005

JON W. DUDAS
*Director of the United States Patent and Trademark Office*

SEQUENCE LISTING (1) GENERAL INFORMATION:

(iii) NUMBER OF SEQUENCES: 118

(2) INFORMATION FOR SEQ ID NO: 1:

(i) SEQUENCE CHARACTERISTICS:
      (A) LENGTH: 14 amino acids
      (B) TYPE: amino acid
      (C) STRANDEDNESS: single
      (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO: 1:

Ala Arg Glu Arg Asp Tyr Arg Leu Asp Tyr Trp Gly Gln Gly
1               5                   10

(2) INFORMATION FOR SEQ ID NO: 2:

(i) SEQUENCE CHARACTERISTICS:
      (A) LENGTH: 17 amino acids
      (B) TYPE: amino acid
      (C) STRANDEDNESS: single
      (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO: 2:

Ala Arg Gly Ala Val Val Ser Tyr Tyr Ala Met Asp Tyr Trp Gly Gln
1               5                   10                  15
Gly

```
(2) INFORMATION FOR SEQ ID NO: 3:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO: 3:

Tyr Ala Val Thr Gly Arg Gly Asp Ser Pro Ala Ser Ser Lys Pro Ile
 1               5                  10                  15

(2) INFORMATION FOR SEQ ID NO: 4:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO: 4:

Tyr Ala Glu Arg Asp Tyr Arg Leu Asp Tyr Pro Ile
 1               5                  10

(2) INFORMATION FOR SEQ ID NO: 5:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO: 5:

Tyr Ala Val Arg Asp Tyr Arg Leu Asp Tyr Pro Ile
 1               5                  10

(2) INFORMATION FOR SEQ ID NO: 6:

(i) SEQUENCE CHARACTERISTICS:
        (A) LENGTH: 16 amino acids
        (B) TYPE: amino acid
        (C) STRANDEDNESS: single
        (D) TOPOLOGY: linear
```

(ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO: 6:

Tyr Ala Val Arg Asp Tyr Arg Leu Asp Tyr Ala Ser Ser Lys Pro Ile
  1               5                  10                  15

(2) INFORMATION FOR SEQ ID NO: 7:

(i) SEQUENCE CHARACTERISTICS:
            (A) LENGTH: 13 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO: 7:

Tyr Ala Val Arg Asp Tyr Arg Leu Asp Tyr Lys Pro Ile
  1               5                  10

(2) INFORMATION FOR SEQ ID NO: 8:

(i) SEQUENCE CHARACTERISTICS:
            (A) LENGTH: 11 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO: 8:

Tyr Ala Val Arg Asp Tyr Arg Ser Lys Pro Ile
  1               5                  10

(2) INFORMATION FOR SEQ ID NO: 9:

(i) SEQUENCE CHARACTERISTICS:
            (A) LENGTH: 14 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO: 9:

Tyr Ala Val Thr Arg Asp Tyr Arg Leu Ser Ser Lys Pro Ile
1               5                   10

(2) INFORMATION FOR SEQ ID NO: 10:

(i) SEQUENCE CHARACTERISTICS:
            (A) LENGTH: 15 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO: 10:

Tyr Ala Val Thr Glu Arg Asp Tyr Arg Leu Ser Ser Lys Pro Ile
1               5                   10                  15

(2) INFORMATION FOR SEQ ID NO: 11:

(i) SEQUENCE CHARACTERISTICS:
            (A) LENGTH: 15 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO: 11:

Tyr Ala Val Ala Val Val Ser Tyr Tyr Ala Met Asp Tyr Pro Ile
1               5                   10                  15

(2) INFORMATION FOR SEQ ID NO: 12:

(i) SEQUENCE CHARACTERISTICS:
            (A) LENGTH: 16 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO: 12:

Tyr Ala Val Thr Ala Val Val Ser Tyr Tyr Ala Ser Ser Lys Pro Ile

```
           1           5          10          15
```

(2) INFORMATION FOR SEQ ID NO: 13:

(i) SEQUENCE CHARACTERISTICS:
        (A) LENGTH: 59 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 13:

```
CGGGATCCCA TATGCAGGTT TCTGATGTTC CGCGTGACCT GGAAGTTGTT GCTGCGACC         59
```

(2) INFORMATION FOR SEQ ID NO: 14:

(i) SEQUENCE CHARACTERISTICS:
        (A) LENGTH: 55 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 14:

```
TAACTGCAGG AGCATCCCAG CTGATCAGCA GGCTAGTCGG GGTCGCAGCA ACAAC             55
```

(2) INFORMATION FOR SEQ ID NO: 15:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 15:

```
CTCCTGCAGT TACCGTGCGT TATTACCGTA TCACGTACGG TGAAACCGGT G                 51
```

(2) INFORMATION FOR SEQ ID NO: 16:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 16:

GTGAATTCCT GAACCGGGGA GTTACCACCG GTTTCACCG                    39

(2) INFORMATION FOR SEQ ID NO: 17:

(i) SEQUENCE CHARACTERISTICS:
            (A) LENGTH: 46 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 17:

AGGAATTCAC TGTACCTGGT TCCAAGTCTA CTGCTACCAT CAGCGG            46

(2) INFORMATION FOR SEQ ID NO: 18:

(i) SEQUENCE CHARACTERISTICS:
            (A) LENGTH: 38 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 18:

GTATAGTCGA CACCCGGTTT CAGGCCGCTG ATGGTAGC                     38

(2) INFORMATION FOR SEQ ID NO: 19:

(i) SEQUENCE CHARACTERISTICS:
            (A) LENGTH: 32 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 19:

CGGGTGTCGA CTATACCATC ACTGTATACG CT                          32

(2) INFORMATION FOR SEQ ID NO: 20:

(i) SEQUENCE CHARACTERISTICS:
        (A) LENGTH: 55 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 20:

CGGGATCCGA GCTCGCTGGG CTGTCACCAC GGCCAGTAAC AGCGTATACA GTGAT       55

(2) INFORMATION FOR SEQ ID NO: 21:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 21:

CAGCGAGCTC CAAGCCAATC TCGATTAACT ACCGT                         35

(2) INFORMATION FOR SEQ ID NO: 22:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 22:

CGGGATCCTC GAGTTACTAG GTACGGTAGT TAATCGA                       37

(2) INFORMATION FOR SEQ ID NO: 23:

(i) SEQUENCE CHARACTERISTICS:
        (A) LENGTH: 38 base pairs (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 23:

CGGGATCCAC GCGTGCCACC GGTACGGTAG TTAATCGA                                    38

(2) INFORMATION FOR SEQ ID NO: 24:

(i) SEQUENCE CHARACTERISTICS:
            (A) LENGTH: 44 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 24:

CGGGATCCAC GCGTCCATTC GTTTGTGAAT ATCAAGGCCA ATCG                             44

(2) INFORMATION FOR SEQ ID NO: 25:

(i) SEQUENCE CHARACTERISTICS:
            (A) LENGTH: 39 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 25:

CCGGAAGCTT TAAGACTCCT TATTACGCAG TATGTTAGC                                   39

(2) INFORMATION FOR SEQ ID NO: 26:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 26:

CTGTTACTGG CCGTGAGATC TAACCAGCGA GCTCCA                              36

(2) INFORMATION FOR SEQ ID NO: 27:

(i) SEQUENCE CHARACTERISTICS:
            (A) LENGTH: 51 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 27:

GATCAGCTGG GATGCTCCTN NKNNKNNKNN KNNKTATTAC CGTATCACGT A             51

(2) INFORMATION FOR SEQ ID NO: 28:

(i) SEQUENCE CHARACTERISTICS:
            (A) LENGTH: 57 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 28:

TGTATACGCT GTTACTGGCN NKNNKNNKNN KNNKNNKNNK TCCAAGCCAA TCTCGAT       57

(2) INFORMATION FOR SEQ ID NO: 29:

(i) SEQUENCE CHARACTERISTICS:
            (A) LENGTH: 47 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 29:

CTGTATACGC TGTTACTGGC NNKNNKNNKN NKCCAGCGAG CTCCAAG                  47

(2) INFORMATION FOR SEQ ID NO: 30:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 30:

CATCACTGTA TACGCTGTTA CTNNKNNKNN KNNKNNKTCC AAGCCAATCT C          51

(2) INFORMATION FOR SEQ ID NO: 31:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO: 31:

Cys Ala Arg Arg Ala
 1               5

(2) INFORMATION FOR SEQ ID NO: 32:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO: 32:

Arg Trp Ile Pro Leu Ala Lys
 1               5

(2) INFORMATION FOR SEQ ID NO: 33:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO: 33:

```
Cys Trp Arg Arg Ala
1               5
```

(2) INFORMATION FOR SEQ ID NO: 34:

(i) SEQUENCE CHARACTERISTICS:
              (A) LENGTH: 7 amino acids
              (B) TYPE: amino acid
              (C) STRANDEDNESS: single
              (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO: 34:

```
Arg Trp Val Gly Leu Ala Trp
1               5
```

(2) INFORMATION FOR SEQ ID NO: 35:

(i) SEQUENCE CHARACTERISTICS:
              (A) LENGTH: 5 amino acids
              (B) TYPE: amino acid
              (C) STRANDEDNESS: single
              (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO: 35:

```
Cys Lys His Arg Arg
1               5
```

(2) INFORMATION FOR SEQ ID NO: 36:

(i) SEQUENCE CHARACTERISTICS:
              (A) LENGTH: 7 amino acids
              (B) TYPE: amino acid
              (C) STRANDEDNESS: single
              (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO: 36:

Phe Ala Asp Leu Trp Trp Arg
 1               5

(2) INFORMATION FOR SEQ ID NO: 37:

(i) SEQUENCE CHARACTERISTICS:
            (A) LENGTH: 5 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO: 37:

Cys Arg Arg Gly Arg
 1               5

(2) INFORMATION FOR SEQ ID NO: 38:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO: 38:

Arg Gly Phe Met Trp Leu Ser
 1               5

(2) INFORMATION FOR SEQ ID NO: 39:

(i) SEQUENCE CHARACTERISTICS:
            (A) LENGTH: 5 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO: 39:

Cys Asn Trp Arg Arg
 1               5

(2) INFORMATION FOR SEQ ID NO: 40:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO: 40:

Arg Ala Tyr Arg Tyr Arg Trp
 1               5

(2) INFORMATION FOR SEQ ID NO: 41:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO: 41:

Ser Arg Leu Arg Arg
 1               5

(2) INFORMATION FOR SEQ ID NO: 42:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO: 42:

Pro Pro Trp Arg Val
 1               5

(2) INFORMATION FOR SEQ ID NO: 43:

(i) SEQUENCE CHARACTERISTICS:
        (A) LENGTH: 5 amino acids
        (B) TYPE: amino acid
        (C) STRANDEDNESS: single

```
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO: 43:

Ala Arg Trp Thr Leu
1               5

(2) INFORMATION FOR SEQ ID NO: 44:

(i) SEQUENCE CHARACTERISTICS:
         (A) LENGTH: 5 amino acids
         (B) TYPE: amino acid
         (C) STRANDEDNESS: single
         (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO: 44:

Arg Arg Trp Trp Trp
1               5

(2) INFORMATION FOR SEQ ID NO: 45:

(i) SEQUENCE CHARACTERISTICS:
         (A) LENGTH: 5 amino acids
         (B) TYPE: amino acid
         (C) STRANDEDNESS: single
         (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO: 45:

Gly Gln Arg Thr Phe
1               5

(2) INFORMATION FOR SEQ ID NO: 46:

(i) SEQUENCE CHARACTERISTICS:
         (A) LENGTH: 5 amino acids
         (B) TYPE: amino acid
         (C) STRANDEDNESS: single
         (D) TOPOLOGY: linear (ii) MOLECULE TYPE: peptide (iii) HYPOTHETICAL: NO (iv) ANTI-SENSE: NO
```

(v) FRAGMENT TYPE: internal (vi) ORIGINAL SOURCE:

(xi) SEQUENCE DESCRIPTION: SEQ ID NO: 46:

Arg Arg Trp Trp Ala
 1               5

(2) INFORMATION FOR SEQ ID NO: 47:

(i) SEQUENCE CHARACTERISTICS:
            (A) LENGTH: 5 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO: 47:

Ala Val Thr Val Arg
 1               5

(2) INFORMATION FOR SEQ ID NO: 48:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO: 48:

Arg Gly Asp Ser Pro Ala Ser
 1               5

(2) INFORMATION FOR SEQ ID NO: 49:

(i) SEQUENCE CHARACTERISTICS:
            (A) LENGTH: 5 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO: 49:

```
Cys Asn Trp Arg Arg
 1               5

(2) INFORMATION FOR SEQ ID NO: 50:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO: 50:

Arg Ala Tyr Arg Tyr Arg Trp
 1               5

(2) INFORMATION FOR SEQ ID NO: 51:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO: 51:

Cys Met Trp Arg Ala
 1               5

(2) INFORMATION FOR SEQ ID NO: 52:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO: 52:

Arg Trp Gly Met Leu Arg Arg
 1               5

(2) INFORMATION FOR SEQ ID NO: 53:

(i) SEQUENCE CHARACTERISTICS:
```

(A) LENGTH: 5 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO: 53:

Ala Arg Met Arg Glu
1               5

(2) INFORMATION FOR SEQ ID NO: 54:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO: 54:

Arg Trp Leu Arg Gly Arg Tyr
1               5

(2) INFORMATION FOR SEQ ID NO: 55:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO: 55:

Cys Ala Arg Arg Arg
1               5

(2) INFORMATION FOR SEQ ID NO: 56:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO: 56:

Arg Arg Ala Gly Trp Gly Trp
  1               5

(2) INFORMATION FOR SEQ ID NO: 57:

(i) SEQUENCE CHARACTERISTICS:
              (A) LENGTH: 5 amino acids
              (B) TYPE: amino acid
              (C) STRANDEDNESS: single
              (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO: 57:

Cys Asn Trp Arg Arg
  1               5

(2) INFORMATION FOR SEQ ID NO: 58:

(i) SEQUENCE CHARACTERISTICS:
              (A) LENGTH: 7 amino acids
              (B) TYPE: amino acid
              (C) STRANDEDNESS: single
              (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO: 58:

Arg Ala Tyr Arg Tyr Arg Trp
  1               5

(2) INFORMATION FOR SEQ ID NO: 59:

(i) SEQUENCE CHARACTERISTICS:
              (A) LENGTH: 5 amino acids
              (B) TYPE: amino acid
              (C) STRANDEDNESS: single
              (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO: 59:

Arg Trp Arg Glu Arg
1               5

(2) INFORMATION FOR SEQ ID NO: 60:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO: 60:

Arg His Pro Trp Thr Glu Arg
1               5

(2) INFORMATION FOR SEQ ID NO: 61:

(i) SEQUENCE CHARACTERISTICS:
            (A) LENGTH: 5 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO: 61:

Cys Asn Trp Arg Arg
1               5

(2) INFORMATION FOR SEQ ID NO: 62:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO: 62:

Arg Ala Tyr Arg Tyr Arg Trp
1               5

(2) INFORMATION FOR SEQ ID NO: 63:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO: 63:

Glu Arg Arg Val Pro
1               5

(2) INFORMATION FOR SEQ ID NO: 64:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO: 64:

Arg Leu Leu Leu Trp Gln Arg
1               5

(2) INFORMATION FOR SEQ ID NO: 65:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO: 65:

Gly Arg Gly Ala Gly
1               5

(2) INFORMATION FOR SEQ ID NO: 66:

(i) SEQUENCE CHARACTERISTICS:
        (A) LENGTH: 7 amino acids
        (B) TYPE: amino acid
        (C) STRANDEDNESS: single
        (D) TOPOLOGY: linear

```
        (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO: 66:

Phe Gly Ser Phe Glu Arg Arg
  1               5

(2) INFORMATION FOR SEQ ID NO: 67:

(i) SEQUENCE CHARACTERISTICS:
             (A) LENGTH: 5 amino acids
             (B) TYPE: amino acid
             (C) STRANDEDNESS: single
             (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO: 67:

Cys Arg Trp Thr Arg
  1               5

(2) INFORMATION FOR SEQ ID NO: 68:

(i) SEQUENCE CHARACTERISTICS:
             (A) LENGTH: 7 amino acids
             (B) TYPE: amino acid
             (C) STRANDEDNESS: single
             (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO: 68:

Arg Arg Trp Phe Asp Gly Ala
  1               5

(2) INFORMATION FOR SEQ ID NO: 69:

(i) SEQUENCE CHARACTERISTICS:
             (A) LENGTH: 5 amino acids
             (B) TYPE: amino acid
             (C) STRANDEDNESS: single
             (D) TOPOLOGY: linear (ii) MOLECULE TYPE: peptide (iii) HYPOTHETICAL: NO (iv) ANTI-SENSE: NO
```

(v) FRAGMENT TYPE: internal (vi) ORIGINAL SOURCE:

(xi) SEQUENCE DESCRIPTION: SEQ ID NO: 69:

Cys Asn Trp Arg Arg
1               5

(2) INFORMATION FOR SEQ ID NO: 70:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO: 70:

Arg Ala Tyr Arg Tyr Arg Trp
1               5

(2) INFORMATION FOR SEQ ID NO: 71:

(i) SEQUENCE CHARACTERISTICS:
            (A) LENGTH: 5 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO: 71:

Ala Val Thr Val Arg
1               5

(2) INFORMATION FOR SEQ ID NO: 72:

(i) SEQUENCE CHARACTERISTICS:
            (A) LENGTH: 5 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO: 72:

Gly Arg Gly Asp Ser

```
     1               5
```

(2) INFORMATION FOR SEQ ID NO: 73:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO: 73:

```
Gly Gln Arg Thr Phe
 1               5
```

(2) INFORMATION FOR SEQ ID NO: 74:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO: 74:

```
Arg Arg Trp Trp Ala
 1               5
```

(2) INFORMATION FOR SEQ ID NO: 75:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO: 75:

```
Gly Gln Arg Thr Phe
 1               5
```

(2) INFORMATION FOR SEQ ID NO: 76:

(i) SEQUENCE CHARACTERISTICS:
        (A) LENGTH: 5 amino acids

```
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO: 76:

Arg Arg Trp Trp Ala
 1               5

(2) INFORMATION FOR SEQ ID NO: 77:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO: 77:

Gly Gln Arg Thr Phe
 1               5

(2) INFORMATION FOR SEQ ID NO: 78:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO: 78:

Arg Arg Trp Trp Ala
 1               5

(2) INFORMATION FOR SEQ ID NO: 79:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (iii) HYPOTHETICAL: NO
```

(iv) ANTI-SENSE: NO (v) FRAGMENT TYPE: internal (vi) ORIGINAL SOURCE:

(xi) SEQUENCE DESCRIPTION: SEQ ID NO: 79:

Leu Arg Tyr Arg Ser
1               5

(2) INFORMATION FOR SEQ ID NO: 80:

(i) SEQUENCE CHARACTERISTICS:
             (A) LENGTH: 5 amino acids
             (B) TYPE: amino acid
             (C) STRANDEDNESS: single
             (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO: 80:

Gly Trp Arg Trp Arg
1               5

(2) INFORMATION FOR SEQ ID NO: 81:

(i) SEQUENCE CHARACTERISTICS:
             (A) LENGTH: 5 amino acids
             (B) TYPE: amino acid
             (C) STRANDEDNESS: single
             (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO: 81:

Gly Gln Arg Thr Phe
1               5

(2) INFORMATION FOR SEQ ID NO: 82:

(i) SEQUENCE CHARACTERISTICS:
             (A) LENGTH: 5 amino acids
             (B) TYPE: amino acid
             (C) STRANDEDNESS: single
             (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO: 82:

Arg Arg Trp Trp Ala
1               5

(2) INFORMATION FOR SEQ ID NO: 83:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO: 83:

Gly Gln Arg Thr Phe
1               5

(2) INFORMATION FOR SEQ ID NO: 84:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO: 84:

Arg Arg Trp Trp Ala
1               5

(2) INFORMATION FOR SEQ ID NO: 85:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO: 85:

Leu Arg Tyr Arg Ser
1               5

(2) INFORMATION FOR SEQ ID NO: 86:

(i) SEQUENCE CHARACTERISTICS:
            (A) LENGTH: 5 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO: 86:

Gly Trp Arg Trp Arg
1               5

(2) INFORMATION FOR SEQ ID NO: 87:

(i) SEQUENCE CHARACTERISTICS:
            (A) LENGTH: 5 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO: 87:

Leu Arg Tyr Arg Ser
1               5

(2) INFORMATION FOR SEQ ID NO: 88:

(i) SEQUENCE CHARACTERISTICS:
            (A) LENGTH: 5 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO: 88:

Gly Trp Arg Trp Arg
1               5

(2) INFORMATION FOR SEQ ID NO: 89:

(i) SEQUENCE CHARACTERISTICS:
            (A) LENGTH: 5 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO: 89:

Gly Gln Arg Thr Phe
1               5

(2) INFORMATION FOR SEQ ID NO: 90:

(i) SEQUENCE CHARACTERISTICS:
             (A) LENGTH: 5 amino acids
             (B) TYPE: amino acid
             (C) STRANDEDNESS: single
             (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO: 90:

Arg Arg Trp Trp Ala
1               5

(2) INFORMATION FOR SEQ ID NO: 91:

(i) SEQUENCE CHARACTERISTICS:
             (A) LENGTH: 5 amino acids
             (B) TYPE: amino acid
             (C) STRANDEDNESS: single
             (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO: 91:

Leu Arg Tyr Arg Ser
1               5

(2) INFORMATION FOR SEQ ID NO: 92:

(i) SEQUENCE CHARACTERISTICS:
             (A) LENGTH: 5 amino acids
             (B) TYPE: amino acid
             (C) STRANDEDNESS: single
             (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO: 92:

Gly Trp Arg Trp Arg
1               5

(2) INFORMATION FOR SEQ ID NO: 93:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 93:

GCAGTTACCG TGCGT                                                                15

(2) INFORMATION FOR SEQ ID NO: 94:

(i) SEQUENCE CHARACTERISTICS:
            (A) LENGTH: 5 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO: 94:

Ala Val Trp Val Arg
1               5

(2) INFORMATION FOR SEQ ID NO: 95:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 95:

GGCCGTGGTG ACAGCCCAGC GAGC                                                      24

(2) INFORMATION FOR SEQ ID NO: 96:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO: 96:

Gly Arg Gly Asp Ser Pro Ala Ser
1            5

(2) INFORMATION FOR SEQ ID NO: 97:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 97:

TCGAGGTTGC GGCGG                                         15

(2) INFORMATION FOR SEQ ID NO: 98:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO: 98:

Ser Arg Leu Arg Arg
1            5

(2) INFORMATION FOR SEQ ID NO: 99:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 99:

CCGCCGTGGA GGGTG                                                     15

(2) INFORMATION FOR SEQ ID NO: 100:

(i) SEQUENCE CHARACTERISTICS:
             (A) LENGTH: 5 amino acids
             (B) TYPE: amino acid
             (C) STRANDEDNESS: single
             (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO: 100:

Pro Pro Trp Arg Val
 1               5

(2) INFORMATION FOR SEQ ID NO: 101:

(i) SEQUENCE CHARACTERISTICS:
             (A) LENGTH: 15 base pairs
             (B) TYPE: nucleic acid
             (C) STRANDEDNESS: single
             (D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 101:

GGTCAGCGAA CTTTT                                                     15

(2) INFORMATION FOR SEQ ID NO: 102:

(i) SEQUENCE CHARACTERISTICS:
             (A) LENGTH: 5 amino acids
             (B) TYPE: amino acid
             (C) STRANDEDNESS: single
             (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO: 102:

Gly Gln Arg Trp Phe
1               5

(2) INFORMATION FOR SEQ ID NO: 103:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 103:

AGGCGGTGGT GGGCT                                               15

(2) INFORMATION FOR SEQ ID NO: 104:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO: 104:

Arg Arg Trp Trp Ala
1               5

(2) INFORMATION FOR SEQ ID NO: 105:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 105:

GCGAGGTGGA CGCTT                                               15

(2) INFORMATION FOR SEQ ID NO: 106:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO: 106:

Ala Arg Trp Thr Leu
1               5

(2) INFORMATION FOR SEQ ID NO: 107:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 107:

AGGCGGTGGT GGTGG                                               15

(2) INFORMATION FOR SEQ ID NO: 108:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO: 108:

Arg Arg Trp Trp Trp
1               5

(2) INFORMATION FOR SEQ ID NO: 109:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO: 109:

Gly Lys Lys Gly Lys
 1               5

(2) INFORMATION FOR SEQ ID NO: 110:

(i) SEQUENCE CHARACTERISTICS:
             (A) LENGTH: 94 amino acids
             (B) TYPE: amino acid
             (C) STRANDEDNESS: single
             (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO: 110:

Val Ser Asp Val Pro Arg Asp Leu Glu Val Val Ala Ala Thr Pro Thr
 1               5                  10                  15

Ser Leu Leu Ile Ser Trp Asp Ala Pro Ala Val Thr Val Arg Tyr Tyr
                20                  25                  30

Arg Ile Thr Tyr Gly Glu Thr Gly Gly Asn Ser Pro Val Gln Glu Phe
            35                  40                  45

Thr Val Pro Gly Ser Lys Ser Thr Ala Thr Ile Ser Gly Leu Lys Pro
        50                  55                  60

Gly Val Asp Tyr Thr Ile Thr Val Tyr Ala Val Thr Gly Arg Gly Asp
65                  70                  75                  80

Ser Pro Ala Ser Ser Lys Pro Ile Ser Ile Asn Tyr Arg Thr
                85                  90

(2) INFORMATION FOR SEQ ID NO: 111:

(i) SEQUENCE CHARACTERISTICS:
             (A) LENGTH: 308 base pairs
             (B) TYPE: nucleic acid
             (C) STRANDEDNESS: single
             (D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 111:

CATATGCAGG TTTCTGATGT TCCGCGTGAC CTGGAAGTTG TTGCTGCGAC CCCGACTAGC      60

CTGCTGATCA GCTGGGATGC TCCTGCAGTT ACCGTGCGTT ATTACCGTAT CACGTACGGT     120

GAAACCGGTG GTAACTCCCC GGTTCAGGAA TTCACTGTAC CTGGTTCCAA GTCTACTGCT     180

ACCATCAGCG GCCTGAAACC GGGTGTCGAC TATACCATCA CTGTATACGC TGTTACTGGC      240

CGTGGTGACA GCCCAGCGAG CTCCAAGCCA ATCTCGATTA ACTACCGTAC CTAGTAACTC      300

GAGGATCC                                                                308

(2) INFORMATION FOR SEQ ID NO: 112:

(i) SEQUENCE CHARACTERISTICS:
        (A) LENGTH: 96 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO: 112:

Met Gln Val Ser Asp Val Pro Arg Asp Leu Glu Val Val Ala Ala Thr
1               5                   10                  15

Pro Thr Ser Leu Leu Ile Ser Trp Asp Ala Pro Ala Val Thr Val Arg
                20                  25                  30

Tyr Tyr Arg Ile Thr Tyr Gly Glu Thr Gly Gly Asn Ser Pro Val Gln
            35                  40                  45

Glu Phe Thr Val Pro Gly Ser Lys Ser Thr Ala Thr Ile Ser Gly Leu
        50                  55                  60

Lys Pro Gly Val Asp Tyr Thr Ile Thr Val Tyr Ala Val Thr Gly Arg
65                  70                  75

Gly Asp Ser Pro Ala Ser Ser Lys Pro Ile Ser Ile Asn Tyr Arg Thr
80                  85                  90

(2) INFORMATION FOR SEQ ID NO: 113:

(i) SEQUENCE CHARACTERISTICS:
        (A) LENGTH: 3 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO: 113:

Arg Gly Asp
1

(2) INFORMATION FOR SEQ ID NO: 114:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO: 114:

```
Met Gly Ser Ser His His His His His His Ser Ser Gly Leu Val Pro
1               5                   10                  15
Arg Gly Ser His
            20
```

(2) INFORMATION FOR SEQ ID NO: 115:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO: 115:

```
Gly Gln Arg Thr Phe Arg Arg Trp Trp Ala
1               5                   10
```

(2) INFORMATION FOR SEQ ID NO: 116:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO: 116:

```
Leu Arg Tyr Arg Ser Gly Trp Arg Trp Arg
1               5                   10
```

(2) INFORMATION FOR SEQ ID NO: 117:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO -continued

```
    (v) FRAGMENT TYPE: internal (vi) ORIGINAL SOURCE:

(xi) SEQUENCE DESCRIPTION: SEQ ID NO: 117:

Cys Asn Trp Arg Arg Arg Ala Tyr Arg Tyr Trp Arg
 1               5                  10

(2) INFORMATION FOR SEQ ID NO: 118:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO: 118:

Ala Arg Met Arg Glu Arg Trp Leu Arg Gly Arg Tyr
 1               5                  10
```